(12) United States Patent
Zolotukhin et al.

(10) Patent No.: US 8,679,837 B2
(45) Date of Patent: Mar. 25, 2014

(54) INDUCIBLE SYSTEM FOR HIGHLY EFFICIENT PRODUCTION OF RECOMBINANT ADENO-ASSOCIATED VIRUS (RAAV) VECTORS

(75) Inventors: Sergei Zolotukhin, Gainesville, FL (US); George Aslanidi, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/262,683

(22) PCT Filed: Apr. 1, 2010

(86) PCT No.: PCT/US2010/029540
§ 371 (c)(1),
(2), (4) Date: Dec. 27, 2011

(87) PCT Pub. No.: WO2010/114948
PCT Pub. Date: Oct. 7, 2010

(65) Prior Publication Data
US 2012/0100606 A1    Apr. 26, 2012

Related U.S. Application Data

(60) Provisional application No. 61/165,994, filed on Apr. 2, 2009, provisional application No. 61/239,775, filed on Sep. 3, 2009.

(51) Int. Cl.
| | |
|---|---|
| *C12N 7/01* | (2006.01) |
| *C12N 15/00* | (2006.01) |
| *C12N 15/09* | (2006.01) |
| *C12N 15/33* | (2006.01) |
| *C12N 15/86* | (2006.01) |

(52) U.S. Cl.
USPC ...... 435/348; 435/69.1; 435/320.1; 424/93.2; 424/93.6

(58) Field of Classification Search
None
See application file for complete search history.

(56) References Cited

U.S. PATENT DOCUMENTS

| | | |
|---|---|---|
| 2004/0197895 A1 | 10/2004 | Kotin et al. |
| 2004/0248288 A1 | 12/2004 | Miller et al. |
| 2006/0166363 A1 | 7/2006 | Aolotukhin et al. |

OTHER PUBLICATIONS

Asladini et al., PNAS, vol. 106, No. 13, pp. 5059-5064, March 31, 2009. An inducible system for highly efficient production of recombinant adeno-associated virus (rAAV) vectors in insect Sf9 cell.

Chen, Mol. Therapy, vol. 16, No. 5, pp. 924-930, Mar. 18, 2008. Intron Splicing-mediated Expression of AAV Rep and Cap Genes and Production of AAV Vectors in Insect Cell.

*Primary Examiner* — Maria Marvich
(74) *Attorney, Agent, or Firm* — Timothy H. Van Dyke; Beusse, Wolter, Sanks, Mora & Maire, P.A.

(57) ABSTRACT

Production of clinical grade gene therapy vectors for human trials remains a major hurdle in advancing cures for a number of otherwise incurable diseases. Disclosed herein are systems based on a stably trans formed insect cell lines harboring helper genes required for vector production. Specifically exemplified are system embodiments that take advantage of DNA regulatory elements from two unrelated viruses—AcMNPV and AA V2. System embodiments utilize rep and/or cap genes either stably transfected in cell lines or which are introduced into cells as an expression cassette in a vector. Rep and cap genes that are designed to remain silent until the cell is infected with a viral vector. Infection with viral initiates rescue/amplification of integrated AAV helper genes resulting in dramatic induction of the expression and assembly of rAAV. The arrangement of this specific embodiment provides high levels of Rep and Cap proteins in every cell thus improving rAAV yields by 10-fold. The described vectors are modular in design and may be utilized for the production of other multiprotein complexes.

9 Claims, 8 Drawing Sheets

US 8,679,837 B2

INDUCIBLE SYSTEM FOR HIGHLY EFFICIENT PRODUCTION OF RECOMBINANT ADENO-ASSOCIATED VIRUS (RAAV) VECTORS

RELATED APPLICATIONS

This application claims the benefit under 35 USC §119(e) of U.S. Ser. No. 61/165,994 filed Apr. 2, 2009 and U.S. Ser. No. 61/239,775 filed Sep. 3, 2009 which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, is named 149USsequencelisting.txt.

INTRODUCTION

High production costs of clinical grade gene therapy vectors remain a major impediment preventing many research laboratories from entering the field. This is especially true for replication-deficient rAAV vectors which are produced, for the most part, by plasmid DNA co-transfection. Only recently, alternative scale-up production protocols such as those utilizing baculovirus expression vectors had been developed. Traditionally, BEVs have emerged as one of the most versatile systems for the protein production. They provide high yield combined with the posttranslational modifications of the proteins. In addition to basic protein production BEVs were utilized for more complicated tasks such as the synthesis of heterologous multiprotein complexes (1), production of a variety of virus-like particles, and for the assembly of gene therapy vehicles such as rAAV vectors (2). The latter strategy utilizes insect cells co-infected with three BEVs, a procedure potentially capable of manufacturing rAAV in 'exa-scale' format (3). While extremely promising, the original protocol had not been widely adopted due to several shortcomings including a requirement for the co-infection with three different helpers Bac-Rep, Bac-VP, and Bac-GOI (gene of interest flanked by AAV inverted terminal repeats). Only recently, H. Chen has reported a significantly improved system where rep and cap helper genes in the respective BEVs incorporated artificial introns (4).

DETAILED DESCRIPTION

Embodiments of the present invention are based on the inventors' development of a novel, simple and efficient system of rAAV production in insect cells. In one embodiment, the system takes advantage of DNA regulatory elements from two unrelated viruses—AcMNPV and AAV2. In a more specific embodiment, the endpoint design may comprise two components: 1) stable Sf9-based cell line incorporating integrated copies of rep and cap genes, and 2) Bac-GOI. Rep and cap genes that are designed to remain silent until the cell is infected with Bac-GOI helper which provides both rAAV transgene cassette and immediate-early (IE-1) transcriptional transregulator. Infection with Bac-GOI initiates rescue/amplification of integrated AAV helper genes resulting in dramatic induction of the expression and assembly of rAAV. The arrangement of this specific embodiment provides high levels of Rep and Cap proteins in every cell thus improving rAAV yields by 10-fold. The described vectors are modular in design and may be utilized for the production of other multi-protein complexes.

According to one embodiment, the invention pertains to a method of producing rAAV in insect cells that includes obtaining a population of cells stably transformed to comprise at least one copy of a polynucleotide sequence encoding a rep gene and at least one copy of a polynucleotide sequence encoding a cap gene; and infecting cells of said population with a vector comprising a polynucleotide sequence that encodes an rAAV transgene and a polynucleotide sequence that encodes a transcriptional transregulator that induces expression of said at least one copy of a polynucleotide sequence encoding a rep gene and at least one copy of a polynucleotide sequence encoding a cap gene.

According to another embodiment, the invention pertains to a population of insect cells transfected with a first polynucleotide sequence with the following components arranged from a 5' to 3' direction: hr2-0.9-RBE - - - rep78 and/or a second polynucleotide sequence comprising the following components arranged from a 5' to 3' direction: hr2-0.9-RBE - - - cap. The inventors have discovered that the proximity of the hr2-0.9 element to the rep78 component may affect the expression of rep78. Inventors have found that the hr2-0.9 component has a higher up-modulation effect if it is 500 bp or more upstream of the rep78 component. In a more specific embodiment, the hr2-0.9 element is 500-1500 base pairs upstream from the rep78 element. The inventors believe that a similar arrangement will produce a higher up modulation effect on cap expression as well. Furthermore, the placement of the hr2-0.9 element upstream to the rep78 results in the production of Rep78 and Rep52.

Figure 5:
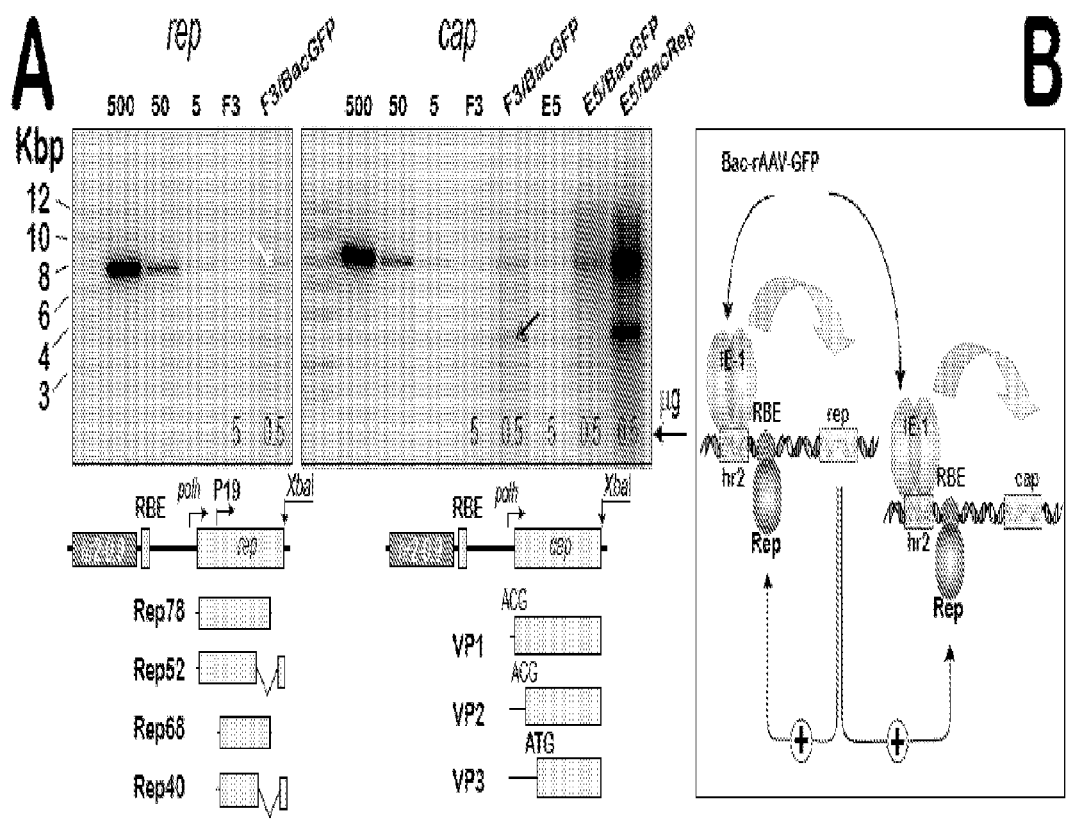
FIG. 5 Analysis of the rescue and amplification of the integrated rep-, and cap genes. A—Southern blotting analysis of the integrated rep and cap genes in F3 (rep/cap) and E5 (cap) stable lines. The parental plasmids were digested with a single cutter (XbaI), per lane amounts loaded were equivalent to 500-, 50-, or 5-copies of the plasmid DNA in 5 μg of chromosomal DNA. Chromosomal DNA samples from uninfected (5 μg, lanes F3 and E5) or BEV-infected (0.5 μg, lanes F3/BacGFP, E5/BacGFP, and E5/BacRep) were digested with XbaI (a single cutter, the positions of the XbaI sites are schematically shown below the respective panels), separated in 1.2% agarose gel, transferred to nylon filter and hybridized to $^{32}$P-labeled rep-, or cap ORF DNA probes (left and right panels, respectively). White double arrowhead shows the form co-migrating with a linearized parent plasmid vector; black double arrowhead indicates a position of a DNA fragment hypothetically derived from the Rep-mediated nicking at the RBE. Rep-, and VP-encoding transcripts and their respective ORFs are diagrammed below the integrating cassettes. B—Diagram depicting a postulated feed forward loop. The transcription of both integrated rep-, and cap genes is induced by BEV-encoded IE-1 transregulator. One of the products, most likely Rep68/78 protein, retorts to interact with RBE inducing rescue/amplification and mediating the transcription.

It is believed that IE-1 trans-regulator induces expression of the rep78 gene via interaction with the hr2-0.9 upstream element (the hr2-0.9 element may include an origin of replication, which as will be discussed below assist in rescue of the rep78 gene thereby resulting in amplification of Rep78). Expressed Rep78 then binds to the RBE which may cause a cleavage of the rep gene. This cleavage event results in a rescue of the rep78 gene which may then replicate within the cell (FIG. 5). It is believed that a similar phenomenon occurs with the second polynucleotide sequence that includes the cap gene (FIG. 5). In an alternative embodiment, the RBE element is omitted from the polynucleotide sequence. Not intended to be bound by any theory, the inventors believe that the BEV-encoded hr2-0.9 element includes an origin of replication. The wtAAV also includes a RBE which results in the rescue and amplification of AAV upon transfection of the cells with a BEV-rAAV-GOI vector.

Abbreviations: TF—transcription factors; AcMNPV—*Autographa californica* multiple nuclear polyhedrosis virus; BEV—baculovirus expression vector; rAAV—recombinant Adeno-associated virus; IE-1—immediate-early transregulator 1; GOI—gene of interest;

Data Deposition Footnote: GenBank Accession #1143868 AAV2 (Accession No. 043303)

SEQ ID NO. 1 represents a polynucleotide sequence of a rep 78 gene that may be implemented to transform cells of interest as described herein.

SEQ ID NO. 2 represents a polypeptide sequence of a Rep78 protein.

SEQ ID NO. 3 represents a polynucleotide sequence of a rep 52 gene that may be implemented to transform cells of interest as described herein.

SEQ ID NO. 4 represents a polypeptide sequence of a rep52 protein.

SEQ ID NO. 5 represents a polynucleotide sequence of a cap gene.

SEQ ID NO. 6 represents a polynucleotide sequence of a cap protein.

SEQ ID NO. 7 represents a polynucleotide sequence of an IE-1 trans-tregulator.

SEQ ID NO. 8 represents a polypeptide sequence of an IE-1 trans-tregulator.

SEQ ID NO. 9 represents an hr2 region from AcMNPV.

Figure 7:
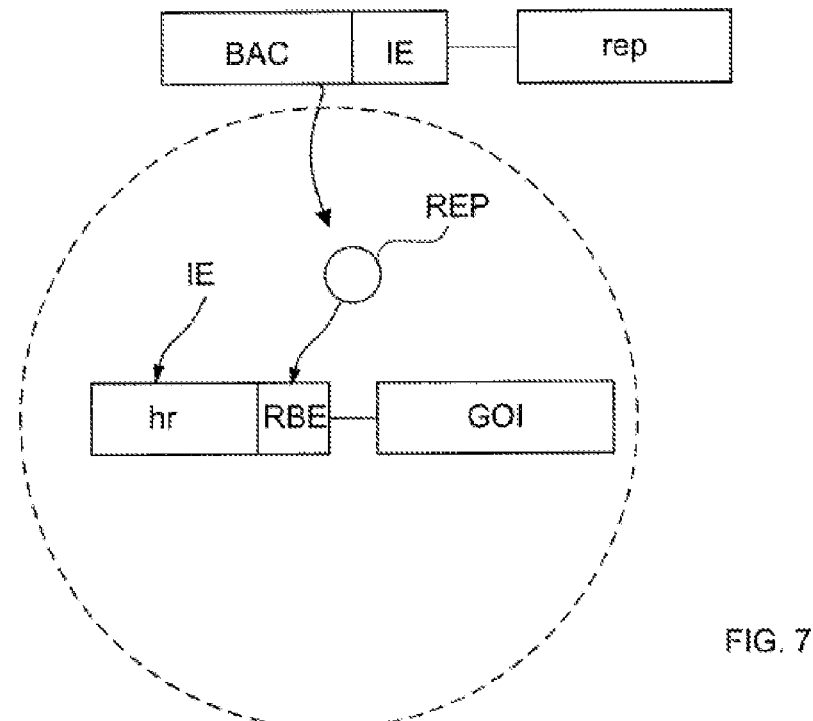
FIG. 7 shows a diagram depicting a proposed arrangement of a system embodiment of the invention.

In another embodiment, the invention pertains to an inducible expression system that comprises an inducer component and a cell component and utilizes at least two of the following elements: hr element, rep gene and product of rep, RBE and GOI. In a specific embodiment, a virus such as BEV is constructed to include an inducer element and a rep gene. The BEV enters cells (shown as dashed line) that have been transformed to include a construct that has, in 5' to 3' direction, an hr element, a RBE, and a GOI. FIG. 7 shows an example of this embodiment. Not to be bound by any particular theory, the inventors believe when the BEV infects the cell and propogates in the cell, the REP protein induces a cut in one strand of the cell genome (or plasmid) harboring the expression cassette. The whole cassette including the hr element is rescued from the cell genome, or a plasmid in the cell, and begins replicating in the cell. This leads to an "amplification" of the expression cassette and the expression of the GOI.

Figure 8:
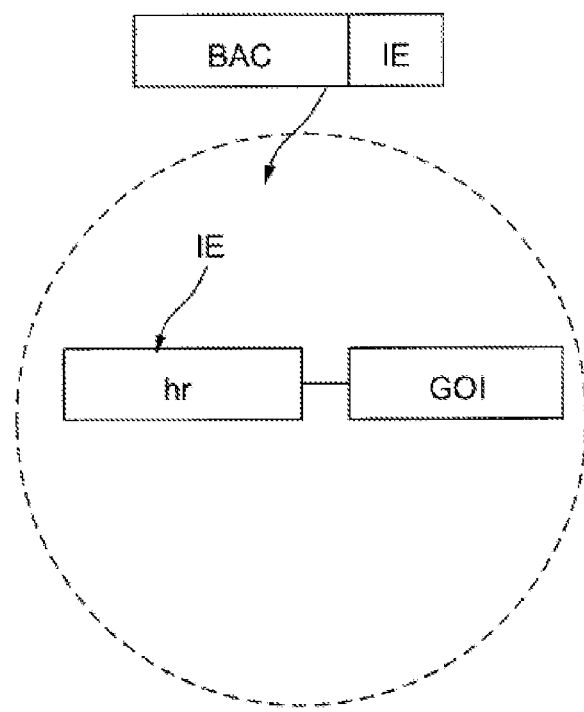
FIG. 8 shows a diagram depicting a proposed arrangement of a system embodiment of the invention.

In another embodiment, the system includes a cell transformed to include a construct that comprises in 5' to 3' direction an hr element and a GOI. A BEV, upon infecting cell (dashed lines), expresses a transactivator, IE-1, that binds to the hr element, which in turn induces expression of GOI. See FIG. 8 for an example of this arrangement.

Figure 9:
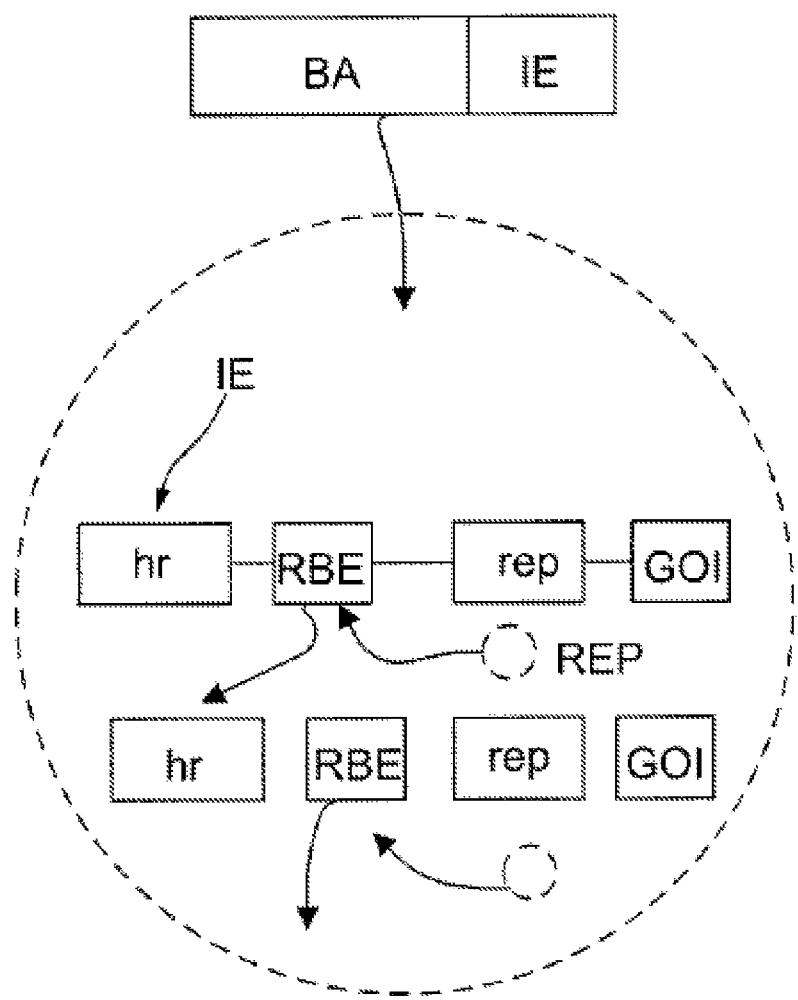
FIG. 9 shows a diagram depicting a proposed arrangement of a system embodiment of the invention.

In a further embodiment, the system includes a cell transformed to include a construct that comprises an hr element, an RBE element, rep gene and GOI. The system also includes a BEV that acts an inducer component. See FIG. 9 for an example of this arrangement. The BEV enters the cell (dashed lines) and expresses a transactivator IE-1, which then interacts with the hr element. This initiates transcription in the expression cassette which involves expression of the rep gene. Expressed REP then binds to the RBE which in turn initiates rescue of the expression cassette from the cell genome and amplification of the expression cassette. While the rep gene is shown upstream of the GOI, the order of the rep gene and GOI should not be critical.

The foregoing proteins and polypeptide sequences, as well as polynucleotides encoding the same, having substantial identity may be used in conjunction with present invention can also be employed in preferred embodiments. Here "substantial identity" means that two sequences, when optimally aligned such as by the programs GAP or BESTFIT (peptides) using default gap weights, or as measured by computer algorithms BLASTX or BLASTP, share at least 50%, preferably 75%, and most preferably 95% sequence identity. Preferably, residue positions which are not identical differ by conservative amino acid substitutions. For example, the substitution of amino acids having similar chemical properties such as charge or polarity are not likely to effect the properties of a protein. Non-limiting examples include glutamine for asparagine or glutamic acid for aspartic acid.

The term "variant" as used herein refers to nucleotide and polypeptide sequences wherein the nucleotide or amino acid sequence exhibits substantial identity with a specified nucleotide or amino acid sequence SEQ ID NO, preferably 75% sequence identity and most preferably 90-95% sequence identity to the sequences of the present invention: provided said variant has a biological activity as defined herein. The variant may be arrived at by modification of the native nucleotide or amino acid sequence by such modifications as insertion, substitution or deletion of one or more nucleotides or amino acids or it may be a naturally occurring variant. The term "variant" also includes homologous sequences which hybridise to the sequences of the invention under standard or preferably stringent hybridisation conditions familiar to those skilled in the art. Examples of the in situ hybridisation procedure typically used are described in (Tisdall et al., 1999); (Juengel et al., 2000). Where such a variant is desired, the nucleotide sequence of the native DNA is altered appropriately. This alteration can be made through elective synthesis of the DNA or by modification of the native DNA by, for example, site-specific or cassette mutagenesis. Preferably, where portions of cDNA or genomic DNA require sequence modifications, site-specific primer directed mutagenesis is employed, using techniques standard in the art.

In specific embodiments, a variant of a polypeptide is one having at least about 80% amino acid sequence identity with the amino acid sequence of a native sequence full length sequence of satiation gut peptides as taught herein and known in the art. Such variant polypeptides include, for instance, polypeptides wherein one or more amino acid residues are added, or deleted, at the N- and/or C-terminus, as well as within one or more internal domains, of the full-length amino acid sequence. Fragments of the peptides are also contemplated. Ordinarily, a variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with a polypeptide encoded by a nucleic acid molecule shown in Attachment B or a specified fragment thereof. Ordinarily, variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, or more.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by those that: (1) employ low ionic strength and high temperature for washing, 0.015 M sodium chloride/0.0015 M sodium citrate/0.1% sodium dodecyl sulfate at 50° C.; (2) employ during hybridization a denaturing agent, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 degrees C.; or (3) employ 50% formamide, 5×SSC (0.75 M NaCl, 0.075 M sodium citrate), 50 mM sodium phosphate (pH 6.8), 0.1% sodium pyrophosphate, 5.times. Denhardt's solution, sonicated salmon sperm DNA (50 μg/ml), 0.1% SDS, and 10% dextran sulfate at 42 degrees C., with washes at 42 degrees C. in 0.2×SSC (sodium chloride/sodium citrate) and 50% formamide at 55 degrees C., followed by a high-stringency wash consisting of 0.1×SSC containing EDTA at 55 degrees C.

"Moderately stringent conditions" are identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37.degree. C. in a solution comprising: 20% formamide, 5×SSC (150 mM NaCl, 15 mM trisodium citrate), 50 mM sodium phosphate (pH 7.6), 5.times. Denhardt's solution, 10% dextran sulfate, and 20 mg/ml denatured sheared salmon sperm DNA, followed by washing the filters in 1.times.SSC at about 37-50 degrees C. The skilled artisan will recognize how to adjust the temperature, ionic strength, etc. as necessary to accommodate factors such as probe length and the like.

Typically, for stringent hybridization conditions a combination of temperature and salt concentration should be chosen that is approximately 12-20° C. below the calculated $T_m$ of the hybrid under study. The $T_m$ of a hybrid between an polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m=81.5°\ C.-16.6(\log_{10}[Na^+])+0.41(\%\ G+C)-0.63(\%\ formamide)-600/l,$$

where l=the length of the hybrid in basepairs.

In a specific embodiment, stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

EXAMPLES

Example 1

Cloning of AcMNPV (Accession No. NC_001623) Homologous Region 2 (hr2)

In order to simplify this system embodiment and reduce the number of components, the inventors sought to derive Sf9-based stable lines expressing AAV rep and cap genes. The challenge of expressing AAV helper genes in the heterologous environment of an insect cell necessitates the use of baculovirus-derived promoters (e.g. polh) which are fully functional only in the context of the whole genome, i.e. next to other viral regulatory elements. Simple cassettes with rep and cap ORFs placed downstream of baculovirus promoters and integrated into the host chromosome, will not achieve similar expression levels as compared to the same modules in the context of a BEVs. Therefore, the inventors set forward to develop a novel modular cassette capable of highest levels of expression when remotely separated from BEV. An additional challenge in constructing such cassettes is that in the wt AAV genome, genes encoded by collinear ORFs within one DNA sequence are transcribed into separate mRNAs from the P5, P19, and P40 promoters. Making three independent integrating modules, each driven by its own promoter, makes the selection process technically complicated.

It was hypothesized that the rep78 ORF could be designed to express both Rep78 and Rep52 hence eliminating the need for a separate vector encoding Rep52 ORF. It was inferred that a BEV-derived enhancer, such as homologous region sequence (hr), could be utilized to increase the transcription rate from wt AAV P19 promoter thus improving the stoichiometry of Rep52/78.

Figure 6:
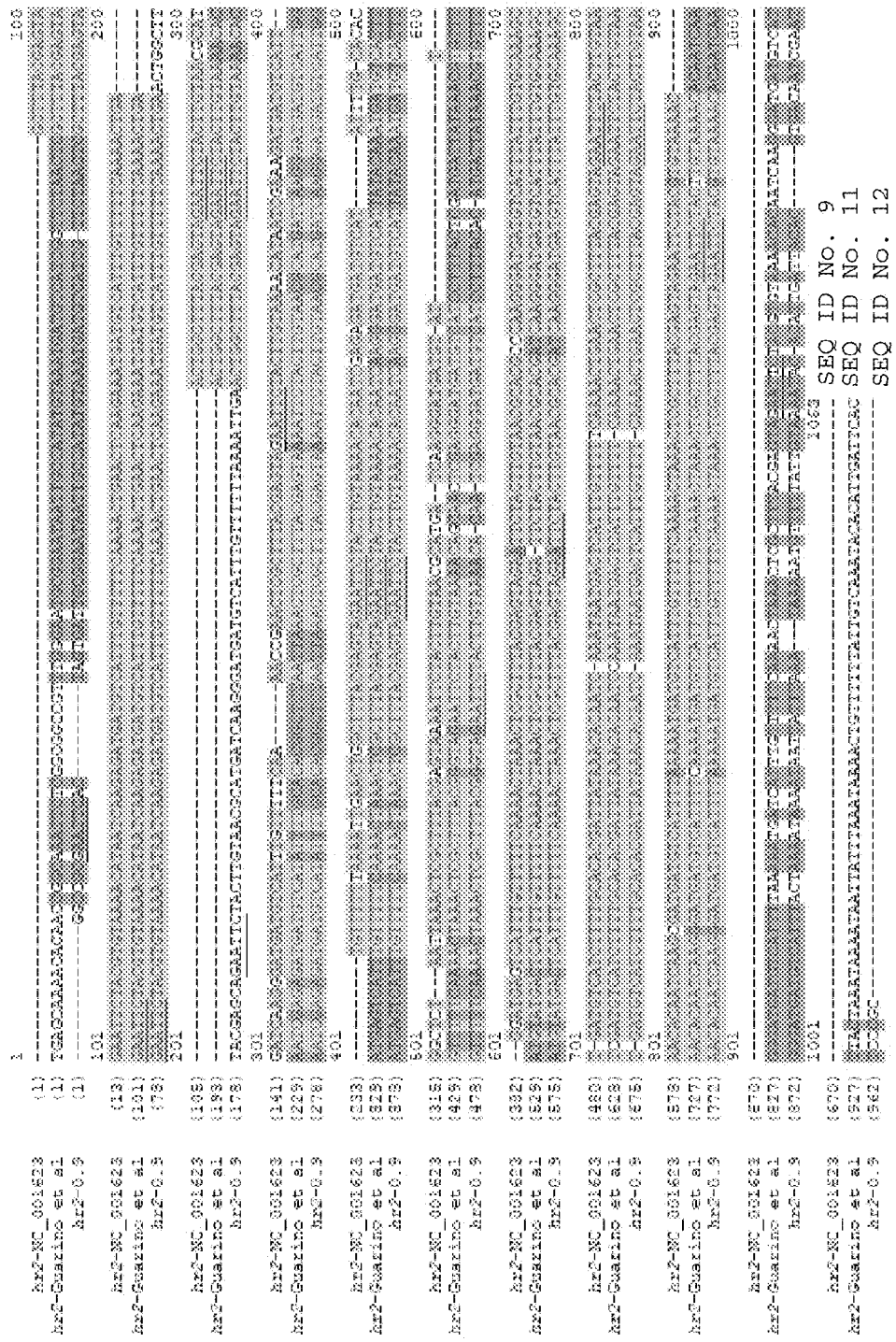
FIG. 6 Alignment of nucleotide sequences of AcMNPV hr2 elements reported in this manuscript (hr2-0.9 SEQ ID NO. 12) and elsewhere (5, 6). Residues in an alignment are colored according to the following scheme: black on white—non-similar residues; blue on cyan—consensus residue derived from a block of similar residues at a given position; red on yellow—consensus residue derived from a completely conserved residue at a given position. Endonuclease EcoRI recognition sites—axes of symmetry of the imperfect palindromes comprising 28 bp IE-1 transregulator-binding element—are underlined.

To test the hypothesis, hr2 was cloned from the wt AcMNPV and its sequence was compared to the other two previously published hr2 sequences (6, 7) (FIG. 6). Our hr2 isolate (hereafter referred as hr2-0.9), although homologous to both reported sequences, showed significant variability, including multiple single nucleotide deletions and insertions, as well as longer stretches such as 72 bp insertion incorporating an additional 28 bp IE-1 binding element.

Example 2

Rep-Expressing Cassettes

Figure 1:
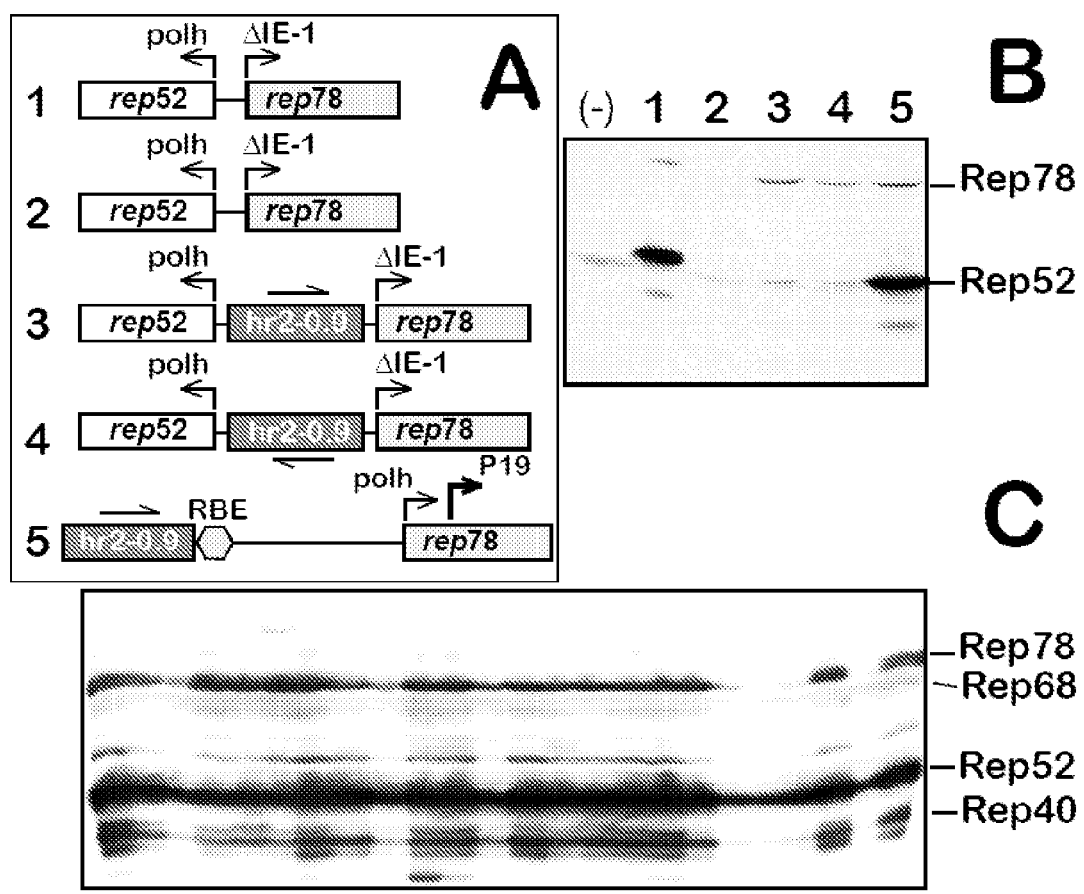
FIG. 1. Expression of rep52/78-encoding cassettes. A—schematic representation of: 1—Rep-expression cassettes in recombinant BEV Bac-Rep from Urabe et al (2); 2—transfer plasmid used to derive Bac-Rep; 3—5-plasmid constructs derived for the current project; polh—late polyhedrin promoter; ΔIE-1—attenuated OpMNPV immediate early promoter (33); P19—wt AAV2 P19 promoter; RBE—Rep-Binding Element (wt AAV2 nt 87-126); leftmost numbers correspond to lanes in panel B. B—Western blotting analysis of Rep52/78 proteins in Sf9 cells after transient transfection with various plasmid DNAs. Cells in the lane marked (−) were mocked-transfected, lane 1—infected with Bac-Rep (MOI of 5), cells in lanes 2-5 were transfected with the respective plasmids shown in panel A and infected with Bac-VP (2) (MOI of 5) to supply transregulator IE-1. C—Western blotting analysis of Rep proteins extracted from individual stable $BSD^R$ cell lines after infection with Bac-VP (MOI of 5) and harvested 72 hr post infection.
Figure 2:
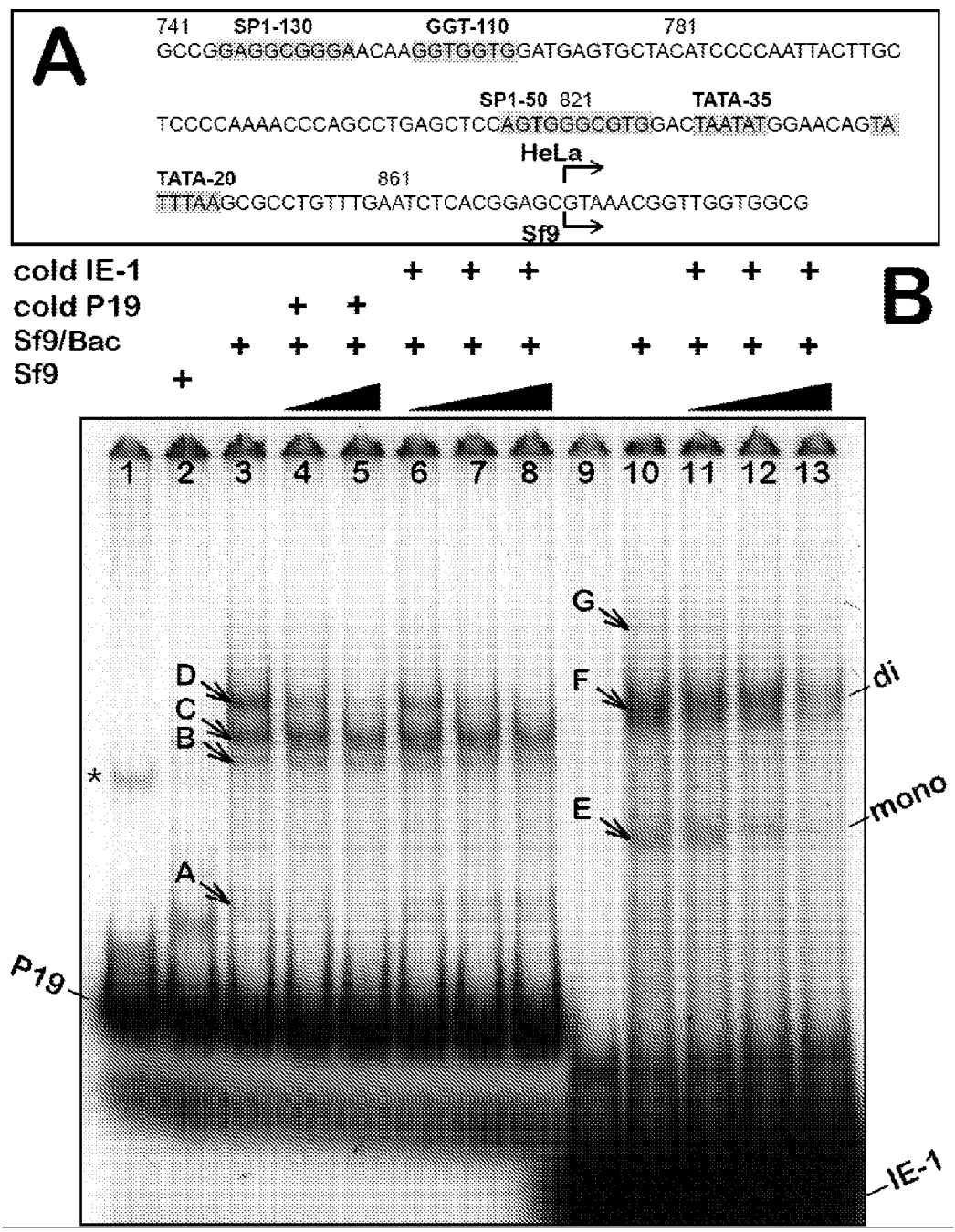
FIG. 2 Analysis of AAV2 P19 promoter activation in Sf9 cells. A—AAV2 P19 promoter nucleotides are indicated above the sequence. Shaded boxes outline sequences with homology to SP1, GGT, and TATA transcription factor binding elements (9, 25). The P19 transcription initiation sites in mammalian (HeLa) and insect cells (Sf9) are indicated by bent arrows. B—EMSA assay. 5'-end-labeled 128 bp PCR fragment of P19 promoter (AAV2 nt 704 to 831, lanes 1 to 8) and 5'-end-labeled IE-1 consensus binding element (34) (lanes 9 to 13) were incubated with crude nuclear extract derived from Sf9 infected with BEV. Samples in the control lanes one and nine contained no nuclear extracts, while in lane 2 the probe was incubated with cell extract from un-infected Sf9. In lanes 4 and 5 $^{32}P$ P19 DNA probe was challenged with unlabeled P19 promoter probe (5- and 15-fold excess, respectively); in lanes 6, 7, and 9 —with unlabeled IE-1 probe (5-, 25-, and 100-fold excess); in lanes 11, 12, and 13 —with unlabeled IE-1 probe (5-, 25-, and 100-fold excess). Different DNA-protein complexes are marked by arrows and labeled with letters. Non-specific DNA band, a by-product of PCR reaction in lane 1 is marked with a (*) symbol. The presumed IE-1 mono-, and dimer/DNA-protein complexes are marked at the right edge of a gel.

To test whether hr2-0.9 could enhance the transcription from wt AAV2 P19 promoter, a series of plasmid vectors (FIG. 1A) were constructed and the expression of rep52 and rep78 genes were tested in a transient transfection assay in insect Sf9 cells. As reported earlier (2), infection of Sf9 cells with Bac-Rep harboring head-to-head rep78 and rep52 genes resulted in the expression of both Rep52 and Rep78 proteins (FIG. 1B, lane 1). The same cassette in the context of a transfer plasmid pFBD-LSR (2) did not produce any Rep proteins (FIG. 2B, lane 2) suggesting a requirement for an enhancer apparently present in a context of Bac-Rep BEV vector carrying Rep-expression cassettes. Insertion of hr2-0.9 between head-to-head polh and □IE-1 promoters created a cassette reminiscent of a transcription control element described earlier (8), with the exception of a hr2-0.9 substituted for hr5. As expected, in the presence of BEV-derived IE-1 transregulator (supplied by helper Bac-VP BEV), the enhancer mediated an expression of both Rep78 and Rep52, the latter one expressed at a lower rate in spite of the fact that it was driven by a considerably stronger polh promoter (FIG. 2B, lane 3). The orientation of hr2-0.9 did not appear to significantly change the expression of either gene (FIG. 2B, lane 4). Because of a limited success in expressing Rep52, we re-designed the vector placing rep78 ORF under control of the late polh promoter while completely removing polh/rep52 cassette. hr2-0.9 was also moved further upstream in order to emulate the context of BEV genome with more distantly positioned hr elements. The inventors discovered that if the hr element is too close to introduce an additional regulatory element upstream of the rep78 ORF, the DNA sequence containing wt AAV2 Rep-binding element (RBE) was inserted. It was shown earlier that either AAV ITR or P5 RBE modulate the expression from P19 promoter (9). In addition, P5 RBE mediated the amplification of integrated adeno-associated virus sequences in mammalian cells (10) thus dramatically improving yields of rAAV production in HeLa-based packaging cell lines. The combination of introduced changes resulted in a dramatic upregulation of the expression of rep52 gene driven by AAV2 P19 promoter (FIG. 2B, lane 5). Therefore, combining regulatory elements from both AAV and BEV in one vector allowed us to achieve an efficient expression of both Rep78 and Rep52 from a single rep78 ORF cassette.

Example 3

Rep-Expressing Stable Cell Lines

For the purpose of rAAV production, stable mammalian cell lines expressing AAV Rep78/52 are notoriously difficult to generate due to the genotoxic effect of the rep component (11). To make a stable line, a complete shutoff of the integrated rep ORF is therefore required. Until now, no similar stable insect cell-based lines expressing AAV rep/cap functions have been reported. Having designed the vector with hr2-0.9-mediated robust expression of both Rep78 and Rep52 in Sf9 cells, the inventors wondered whether the Rep-expression cassette could be utilized to derive stable cell lines.

The plasmid pIR-rep78-hr2-RBE (#5 in FIG. 1A), in addition to Rep expression cassette was constructed to harbor OpIE1 viral promoter-driven bsd (blasticidin S deaminase) gene conferring resistance to blasticidin S. This plasmid had been used to transfect Sf9 cells and select for BS-resistance to derive 24 individual stable cell lines. Remarkably, all analyzed $BS^R$ cell lines, upon infection with Bac-VP BEV, showed expression of both Rep proteins albeit at different levels and at variable stoichiometric ratios (FIG. 1C).

Example 4

Analysis of AAV2 P19 Promoter in Sf9 Cells

Without being limited to any theory, induced expression of rep52 suggested two possibilities: 1) a read-through activation from the upstream polh promoter similar to Adenovirus type 5 early region 1 transcription (12); and 2) activation by elements present within the P19 promoter itself. To distinguish between these two mechanisms, we mapped the transcription initiation site of integrated rep gene from a rep/cap stable $BS^R$ line F3. Using RLM-RACE protocol, the transcription of rep52 gene was determined to be initiated at AAV2 nt 874 (FIG. 2A), i.e. exactly at the same position as in mammalian cells. Therefore, it appeared that the upstream hr2-0.9 directed host cell and BEV-encoded factors to initiate strong transcription from the heterologous P19 promoter.

It was further hypothesized that BEV-encoded immediate early transactivator IE-1 mediates the induction of P19 transcription by interacting with other transcription factors (TF) upstream of P19. To elucidate the mechanism, an EMSA using 128 bp P19 PCR fragment was performed which excluded both TATA-35 and TATA-20 sites. Little if any binding was detected in extracts from uninfected Sf9 cells (FIG. 2B, lane 2). On the contrary, extracts from BEV-infected Sf9 cells formed multiple DNA-protein complexes with P19 promoter (FIG. 2B, lane 3). Some of these complexes (for example, doublet band marked 'A') were not associated with IE-1, as demonstrated by competitive binding to unlabeled P19 probe (lanes 4 and 5) as opposed to the absence of such competition by IE-1 consensus binding element (lanes 6 to 8). The other complexes, such as band 'D', were clearly IE-1-specific as they were outcompeted by both with P19 and IE-1 probes. Complexes 'B' and 'C' were partially competed with 100-fold excess of IE-1 (lane 8) while 15-fold excess of p19 in lane 5 might not have been sufficient to significantly reduce the intensity of these bands.

Lanes 9-13 demonstrate the specificity of IE-1 consensus element in binding: three DNA-protein complexes ('E', 'F', and 'G') are specifically competed with un-labeled IE-1. Two lower bands presumably consist of mono-, and dimer forms of IE-1 (13) while the upper complex 'G' might represent an IE-1 dimer bound to another TF. Therefore, the Rep-expressing integrating cassette provides multiple TF binding sites thus emulating the regulation of the transcription in wt AAV2 genome expressing Rep78/52 and Rep68/40 from a single rep78 ORF.

Example 5

Cap-Expressing Cassettes

Figure 3:
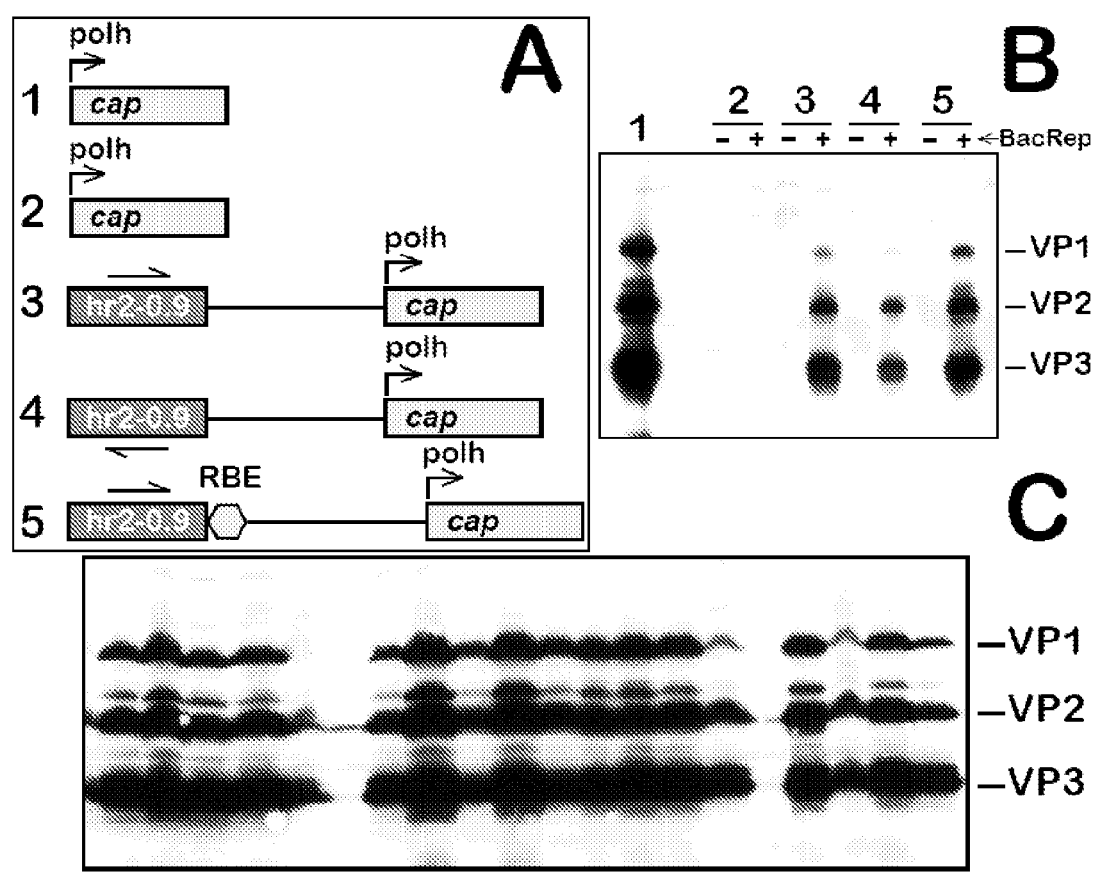
FIG. 3. Expression of AAV2 cap-encoding cassettes. A—schematic representation of: 1—cap expression cassette in BacVP as described by Urabe et al (2); 2—same cassette in a shuttle plasmid backbone; 3-5—plasmid constructs derived for the current project. Genetic element designations are the same as in the FIG. 2 legend. The leftmost numbers correspond to lanes in panel B. B—Western blotting analysis of VP proteins in Sf9 cells after transient transfection with various plasmid DNAs. Cells in lane 1 were infected with BacVP (MOI of 5), cells in lanes 2-5 were transfected with the respective plasmids (FIG. 3A) and either infected (+), or not infected (−) with Bac-Rep (2) (MOI of 5) to supply transregulator IE-1 and Rep78. C—Western blotting analysis of VP proteins extracted from individual stable $BSD^R$ cell lines after infection with Bac-Rep (MOI of 5) and harvested 72 hr post infection.

Using the same plasmid backbone and same regulatory elements, a series of vectors were constructed to express AAV2 cap gene encoding structural proteins VP1, VP2, and VP3 (FIG. 3A). Similarly to rep cassette, the presence of hr enhancer element was required for the cap gene to be expressed: same polh-driven cap ORF was either strongly expressed in the context of BEV Bac-VP (2) (FIG. 3B, lane 1) or was completely silent in the plasmid backbone, regardless whether IE-1 is supplied in trans by BEV (FIG. 3B, lanes 2+/−). Adding hr2-0.9 element upstream resulted in the induction of VPs expression but only in the presence of BEV infection (FIGS. 3A, B, lanes 3+/−). The requirement for IE-1 appears to be absolute as we were unable to detect the expression of VPs in either of the constructs if transiently transfected cells were not infected with Bac-Rep helper (FIG. 3B, all lanes marked by "−" symbol). We have also observed a slight orientational effect of hr2-0.9 (compare lanes 3+ and 4+ in FIG. 3B). In the presence of RBE the VP expression appears to be also enhanced (lanes 3+ vs 5+).

pIR-VPm11-hr2-RBS (vector #5 in FIG. 3A) was used to derive twenty $BS^R$ stable cell lines selected and propagated similar to Rep-expressing lines. Upon induction of cap gene with BacRep BEV infection, the majority (18 out of 20) of lines expressed VP1, VP2, and VP3 structural proteins of AAV2 (FIG. 3C).

Example 6

Rep/Cap-Packaging Stable Cell Lines

Figure 4:
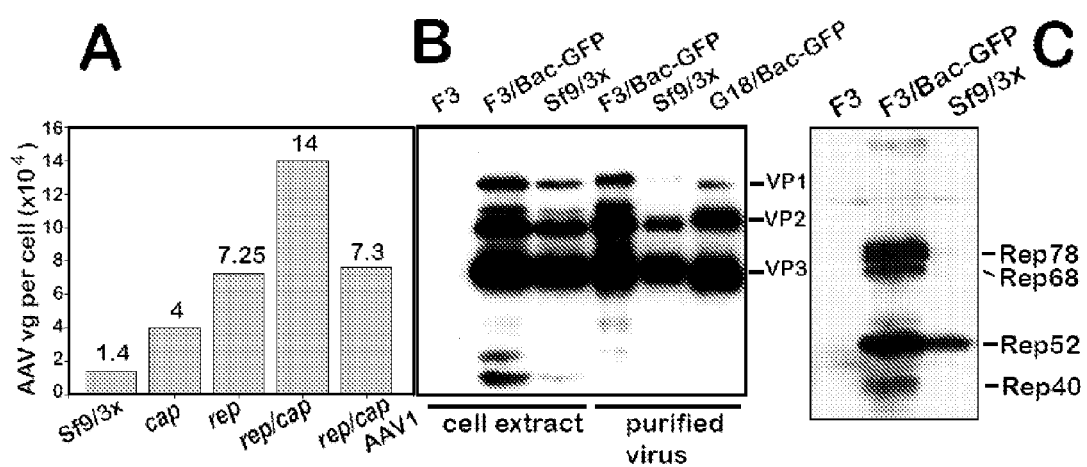
FIG. 4. Characterization of rep/cap packaging cell lines F3 and G18. A—Average yields of purified rAAV-GFP tabulated in vector genomes per cell. Typical run was conducted in 100 ml suspension culture, cells were infected with BEVs at M.O.I. of 3: for Sf9 cells—with 3 BEV helpers (2); for cap stable cell line—with Bac-Rep and Bac-rAAV-GFP; for rep stable line—with Bac-VP and Bac-rAAV-GFP; for AAV2 (F3) and AAV1 (G18) rep/cap packaging line—with Bac-rAAV-GFP. rAAV-GFP was purified as described earlier (35). Four runs per cell line had been conducted. B—Western blotting analysis of AAV2 and AAV1 VP capsid proteins in crude lysates and purified rAAV-GFP. VP protein content in un-infected packaging line F3 (lane F3), F3 infected with Bac-rAAV-GFP (next lane) were compared to Sf9 cells infected with three BEV helpers (SD/3×). Crude lysates and purified rAAV-GFP were analyzed. C—Western blotting analysis of Rep proteins in crude lysates in F3, F3—infected with Bac-rAAV-GFP, and Sf9 cells infected with three BEVs.

To derive Rep/VP-expressing lines, cells were co-transfected with the respective Rep-, and Cap-expressing plasmids and $BS^R$ clones were derived. Twenty individual rep/cap packaging cell lines were screened for their capacity to produce rAAV-GFP upon infection with Bac-rAAV-GFP helper (data not shown). One (designated as F3) was selected for the further analysis and for the production of rAAV. The yields of the purified vectors derived using F3 packaging cells were on average, $1.4 \times 10^5$ drp per cell. This yield exceeded the yield of a triple infection protocol by 10-fold (FIG. 4A).

Because the described vectors are modular in design, the same control elements could be utilized for the expression of other AAV serotypes capsid proteins. In particular, we have also constructed AAV2 rep-AAV1 cap stable cell line dubbed G18. The analysis of the purified GFP-expressing AAV1 vector capsid composition and the yield is shown in FIGS. 4B and 4A, respectively.

To characterize the mechanism of the higher yields, the amount of Rep and VP proteins synthesized in F3 cell line were analyzed. There was no detectable expression of VP (FIG. 4B, lane F3) or Rep (FIG. 4C, lane F3) proteins in uninfected F3 cells followed by the dramatic increase of the expression of both genes induced by Bac-GFP infection. At the time of harvest, the concentration of Cap proteins in F3 was 2-3 times higher than in triple-infected Sf9 cells (FIG. 4B, lane F3/Bac-GFP vs Sf9/3x), while the amounts of Rep proteins, especially Rep78 were overwhelmingly higher compared to SF9 cells co-infected with three BEV helpers (FIG. 4C).

Example 7

Integrated Rep and Cap Genes are Amplified by BEV Infection

The mechanism of the induction of the expression of the integrated helper genes was investigated by analyzing total DNA isolated from stable F3 (rep/cap) and E5 (cap) cell lines (FIG. 5). Southern blotting in conjunction with RT-PCR assays were used to estimate the number of integrated copies. In uninfected cells from rep/cap line F3, two copies of rep and four copies of cap genes were documented (Table 1, FIG. 5, lanes marked F3). Although RT-PCR data indicated less than two rep copies (1.47 copies) per cell, the DNA hybridization pattern revealed that at least two copies of the rep gene were integrated as a head-to-tail concatemer producing, upon digestion with a single cutter XbaI, a monomer fragment of the exact size of the linearized vector (FIG. 5). At 72 hrs post infection with Bac-rAAV-GFP (MOI of 3), the number of copies of rep and cap genes increased up to 57 and 211, respectively (Table 1, FIG. 5, lanes marked F3/BacGFP). This further exhibits that a portion of the amplified molecular structures apparently incorporated a head-to-tail concatemers (FIG. 5, white double arrowhead). A lower discrete band of about 3.6 Kbp (FIG. 5, black double arrowhead) is equimolar to the upper band, suggesting that it could be junction fragment of the integrated concatemers in the amplified structure. It should be noted that the size of this fragment is equivalent to the distance between XbaI recognition site and an RBE site upstream which might indicate a Rep-dependent mechanism of the rescue and amplification. Indeed, in the absence of Rep (FIG. 5, lane E5/BacGFP), when cap-containing E5 cells are infected with Bac-rAAV-GFP, the lower band no longer appears in the rescued structure. When Rep was driven by the immediate early promoter DIE-1 (as in Bac-Rep helper), the effect of total and Rep-mediated amplification was much stronger boosting cap copy number per cell almost up to 1,200 (Table 1, FIG. 5, lane E5/BacRep). The precise molecular mechanism of the rescue/amplification is currently under investigation.

Discussion Related to Examples 1-7

While extremely promising, the original protocol of rAAV production in Baculovirus system had not been widely adopted. One of the main reasons is the complexity of the system involving three independent BEV helpers. According to the Poisson distribution (14), at the optimal multiplicity of infection (MOI) of 3 (15), 95% of cells are infected with at least one BEV, but only 22.4% of cells are infected with 3 particles. At the higher MOIs this ratio reduced even further: for example, at MOI of 9 only 12.5% cells are infected with 9 particles. For rAAV production, cells are infected with the combination of three different BEVs, and the fraction of cells infected with all three helpers at the optimal stoichiometric ratio apparently is even lower (16). For example, solving the Poisson distribution for a particular combination of individual BEV helpers (e.g., 3:3:3) predicts the ratio of respectively infected cells to be only 1.1%. The specifics of rAAV production also requires a coordinated and timely expression of seven helper Rep and Cap proteins at the optimal stoichiometry (2, 5, 16, 17). Adding to the complexity of the system is the fact of the apparent instability of the recombinant BEVs, especially Bac-Rep helper (5). In essence, rAAV production in insect cells poses technical challenges that are quite different from the basic protein manufacturing. We sought to reduce the complexity by deriving packaging stable cell line incorporating rep and cap helper genes. To this end, we utilized one of the critical genetic elements of the AcMNPV—homologous region. Earlier Habib et al. have reported that AcMNPV hr1 enhances transcription from the polyhedrin promoter in a classic enhancer-like manner (18). Other BEV hrs have also been shown to display a potent enhancer function on exogenous and endogenous promoters in the absence of any viral transactivator suggesting that the binding of host factors might be involved in the enhancer mechanism (19). Considering the enhancing propensity of hrs to mediate transcription even without BEV-encoded IE-1 factor, one would predict some basal level of transcription from the integrated rep genes. However, it appears that we have achieved a complete expression shutoff of both rep and cap ORFs positioned downstream of hr2-0.9 in the absence of BEV infection.

The mechanism by which DNA binding promotes IE-1 transactivation is unknown. Olson et al., hypothesized that DNA binding is required for conformational changes in IE-1, a pre-requisite to subsequent interaction with other transcription factors and trans stimulation (13). However, binding to hr alone is insufficient for IE-1-mediated enhancer activity (20-22). Here, we show that upon infection with BEV, several proteins form complexes with P19 promoter, and some of these complexes apparently incorporate IE-1. It is unlikely that IE-1 directly binds to P19 as we were unable to identify canonical IE-1 binding element within the tested P19 fragment. More likely, hr-bound IE-1 interacts with Sf9 host cell factors such as SP1 described recently in Sf9 cells, a transcription factor that was also shown to be capable of binding to the canonical SP1-response element from mammalian cells (23, 24). Incidentally, two SP1-binding sites (SP1-130 and SP1-50, FIG. 2A) were shown to be involved in regulation of transcription from AAV2 P19 promoter (9, 25). Hence, our working model of P19 activation includes insect host cell SP1 and BEV IE-1 bound to their respective response elements within P19 and hr2-0.9. Bound factors subsequently form a trans-activation complex via bent and looped-out DNA similar to what was described for AAV2 P5/P19 interaction (9, 26).

Interestingly, it appeared that the induced rep gene generated a complete set of Rep proteins including smaller Rep68 and Rep40, products of the spliced P5- and P19-derived transcripts. This seems to be a plausible scenario as splicing does occur for BEV-encoded ie-1 transcripts generating another immediate-early transregulator IE-0 (27). Moreover, even AAV2 rep-, and cap-derived transcripts undergo splicing in Sf9 cells infected with BEVs (4). The Rep- and VP-expressing cassettes, therefore, emulate wt AAV genome utilizing hr and RBE DNA elements to upregulate the internal P19 promoter allowing high level expression of the smaller Rep isoforms while still relying on non-canonical ACG start codon for VP1 initiation (FIG. 5A).

One of the advantageous features of the described system is its propensity to rescue and amplify the integrated genes up to 1200 copies per cell. The precise molecular mechanism of such amplification is a subject of a separate study. Nevertheless, it is clear that a feed forward loop is initiated whereby Rep protein encoded by the integrated rep genes interacts with RBE to further enhance the helper cassette amplification and expression (FIG. 5B). Moreover, Rep might take part in the transcription initiation complex mediating P19 promoter activity in conjunction with IE-1. Although Rep is an integral part of rAAV production, the system can efficiently function without Rep protein (FIG. 5, Table 1) suggesting that its modular design could be utilized not only for the production of other AAV serotypes but for unrelated multiprotein complexes as well.

In conclusion, we have designed a simple inducible expression system consisting of only two components: stable Sf9-based cell line and a single BEV. To this end, we utilized, in unconventional way, two genetic elements—hr2 from AcMNPV and RBE from AAV2 providing inducible expression of polh-driven rep78/68 and cap helper genes as well as P19-driven rep52/40. The arrangement provided 10-fold higher yield of rAAV vectors compared to the original triple infection protocol.

Materials and Methods Related to Examples 1-7

Cloning of AcMNPV Homologous Region 2 (hr2).

Wild type AcMNPV was prepared as described previously (28) and the DNA sequence of hr2 [AcMNPV complete genome, nt 26293-26961 GenBank accession #NC_001623, (7)] was amplified using PCR-mediated protocol (Suppl. 2). The band was cloned into pGEM-TEasy and sequence-verified (GenBank accession #1143868).

Mapping 5'-End of Rep52 Transcript.

We utilized RNA Ligase Mediated Rapid Amplification of cDNA Ends (RLM-RACE) kit (Ambion). Cells from rep/cap $BS^R$ line F3 were propagated at $2 \times 10^6$ cells/ml and infected with recombinant Bac-rAAV-GFP (MOI of 5). Seventy-two hrs post-infection, cells were harvested and total RNA was isolated. AAV-specific primers (Suppl. 2) were used in conjunction with 5'RACE Outer and Inner Control primers were provided with the kit. The resulting PCR fragment was subcloned into pGEM-TEasy plasmid (Promega) and 10 random clones were sequenced.

Baculovirus Titering.

BEV titers were determined by qPCR assay developed in our laboratory. The assay is an adaptation of an alkaline PEG-based method for direct PCR (29). Briefly, 5 µl of baculovirus stock is added to 95 µl of alkaline PEG solution (PEG 200, pH 13.5) prepared as descried earlier (29). After vortexing, the sample is incubated at room temperature for 15 min and then diluted 5-fold by adding 0.4 ml $H_2O$. Five µl of this diluted mixture was used directly in RT-PCR 25 µl reaction mixture containing 12.5 µl SybrGreenER and 1.5 µl of 5 µM primers (Suppl. 2). The sample is assayed side-by-side with a serially diluted reference standard, a BEV of a known titer. The amplified sequence is part of AcMNPV gene Ac-IE-01, locus tag—ACNVgp142, a putative early gene transactivator; the size of the amplified DNA fragment is 103 bp.

Construction of Sf9 Stable Cell Lines.

To select and propagate cell lines procedures previously described were followed (30). Blasticidin selection (25 µg/ml) was used for three weeks after which antibiotics were omitted from the media and cells were maintained in regular SFM. To construct cell lines expressing all wt AAV2 proteins, Sf9 cells were co-transfected with undigested pIR-rep78-hr2-RBE and pIR-VPm11-hr2-RBE at the molar ratio of 1:2.5. In-house liposomes were used for the transfection. Screening for the most efficient packaging rep/cap cell line had been performed with $10^6$ cells from each clonal line infected with Bac-rAAV-GFP. At 72 hr post-infection, cell were harvested and subjected to two freeze/thaw cycles. Aliquots of the lysates were used to infect 293 cells. Rep-, and cap lines were picked randomly and the protein expression had been analyzed by Western blotting analysis in cells infected with BEV (Bac-rAAV-GFP for rep- and Bac-Rep for cap lines).

RNA Isolation.

Total RNA from Sf9 cells was isolated by using TRIzol reagent (Invitrogen,) following on-column of DNA digestion and concentration by using RNase-Free DANase Set and RNeasy Mini Elute Cleanup Kit (Qiagen Inc, Valencia, Calif.). RNA integrity was verified by agarose gel (1.2%) electrophoresis with EtBr staining.

Western Blot Analysis.

Sf9 cells growing in SFM media in suspension were harvested by centrifugation, washed with ice-cold PBS and resuspended in lysis buffer containing 50 mM Tris HCl, pH7.5, 120 mM NaCl, 1% Nonidet P-40, 10% glycerol, 10 mM $Na_4P_2O_7$, 1 mM phenyl-methylsulfonyl fluoride (PMSF), 1 mM EDTA, and 1 mM EGTA supplemented with Protease Inhibitor Cocktail (Set 3) (Calbiochem, San Diego, Calif.). The suspension was incubated on ice for one hr and clarified by centrifugation for 30 min at 14000 rpm, 4° C. Normalized for protein concentration samples were separated using 12% PAAG/SDS electrophoresis, transferred to a nitrocellulose membrane, and probed with the anti-cap B1 monoclonal antibodies (1:4000, generously donated by Dr. Muzyczka or anti-Rep 11F monoclonal antibodies (1:4000, a gift from Dr. Muzyczka), following by ECL Anti-mouse IgG, horse radish peroxidase-linked, secondary antibodies (1:1000, Amersham Biosciences, Littele Chalfont Buckinghamshire, UK).

Electrophoretic Mobility Shift Assay (EMSA).

EMSA was carried out as described previously (31). In brief, un-infected, or BEV-infected (72 hr post infection) Sf9 cells were harvested at $2 \times 10^6$ cells/ml and washed with ice-cold PBS. Packed cells were resuspended in 5 volumes of hypotonic buffer (10 mM HEPES, p117.9; 1.5 mM $MgCl_2$; 10 mM KCl; 0.2 mM PMSF; 0.5 mM DTT) and allowed to swell on ice for 10 min. Following homogenization in a glass Dounce, nuclei were collected by centrifugation 15 min at 3300×g. The nuclei were then resuspended in high salt buffer containing 20 mM HEPES, pH7.9; 1.5 mM $MgCl_2$; 0.7 M KCl; 0.2 mM EDTA; 0.2 mM PMSF; 0.5 mM DTT; 25% glycerol. Nuclei were allowed to extract for 30 min on ice and pelleted for 30 min at 25,000×g. Aliquots of the supernatant were flash-frozen in liquid nitrogen. Binding reactions (20 µl) containing 50 fmol $^{32}P$-labeled DNA probe; 1 µg poly(dI-dC); 20 mM HEPES, pH7.9; 100 mM KCl; 1 mM EDTA; 1 mM DTT, 12% glycerol and 60 µg nuclear extract were incubated for 30 min at 27° C. In some instances, unlabeled DNA fragments were added into the assay for competition binding. Non-denaturing 4% PAAG (40:1 acrylamide/bisacrylamide) containing 2.5% glycerol was ran in 0.5×TBE at 30 mA for 2 hr, the gel was transferred on DEAE filter paper, dried, and exposed to X-ray film.

DNA Isolation and RT PCR.

Total DNA from approximately $5 \times 10^6$ cells was isolated using DNeasy Blood & Tissue Kit (Qiagen Inc, Valencia, Calif.). One hundred ng of DNA was used for the quantification analysis by RT-PCR. DNA was amplified by using SYBR GreenER qPCR Supermix (Invitrogen, Carlsbad, Calif.) and the specific primers (Suppl. 2). For the calculations of the integrated gene copy number, the size of Sf9 genome was assumed to be 400 Mb (32).

REFERENCES

1. Berger, I., Fitzgerald, D. J. & Richmond, T. J. (2004) Baculovirus expression system for heterologous multiprotein complexes *Nat Biotechnol* 22, 1583-7.

2. Urabe, M., Ding, C. & Kotin, R. M. (2002) Insect cells as a factory to produce adeno-associated virus type 2 vectors *Hum Gene Ther* 13, 1935-43.
3. Cecchini, S., Negrete, A. & Kotin, R. M. (2008) Toward exascale production of recombinant adeno-associated virus for gene transfer applications *Gene Ther* 15, 823-30.
4. Chen, H. (2008) Intron splicing-mediated expression of AAV Rep and Cap genes and production of AAV vectors in insect cells *Mol Ther* 16, 924-30.
5. Kohlbrenner, E., et al. (2005) Successful production of pseudotyped rAAV vectors using a modified baculovirus expression system *Mol Ther* 12, 1217-25.
6. Guarino, L. A., Gonzalez, M. A. & Summers, M. D. (1986) Complete Sequence and Enhancer Function of the Homologous DNA Regions of *Autographa californica* Nuclear Polyhedrosis Virus *J Virol* 60, 224-229.
7. Ayres, M. D., et al. (1994) The complete DNA sequence of *Autographa californica* nuclear polyhedrosis virus *Virology* 202, 586-605.
8. Jarvis, D. L., Weinkauf, C. & Guarino, L. A. (1996) Immediate-early baculovirus vectors for foreign gene expression in transformed or infected insect cells *Protein Expr Purif* 8, 191-203.
9. Lackner, D. F. & Muzyczka, N. (2002) Studies of the mechanism of transactivation of the adeno-associated virus p19 promoter by Rep protein *J Virol* 76, 8225-35.
10. Nony, P., et al. (2001) Novel cis-acting replication element in the adeno-associated virus type 2 genome is involved in amplification of integrated rep-cap sequences *J Virol* 75, 9991-4.
11. Zolotukhin, S. (2005) Production of recombinant adeno-associated virus vectors *Hum Gene Ther* 16, 551-7.
12. Shen, L. & Spector, D. J. (2003) Local character of readthrough activation in adenovirus type 5 early region 1 transcription control *J Virol* 77, 9266-77.
13. Olson, V. A., Wetter, J. A. & Friesen, P. D. (2003) The highly conserved basic domain I of baculovirus IE1 is required for hr enhancer DNA binding and hr-dependent transactivation *J Virol* 77, 5668-77.
14. Devore, J. L. (2004) *Probability and Statistics for Engineering and the Sciences* (Brooks/Cole Pub Co—Thomson Learning, Belmomt, Calif.).
15. Nielsen, L. K. (2000) *Virus production from cell culture, kinetics*. (Wiley, Mississauga, Ontario, Canada).
16. Aucoin, M. G., Perrier, M. & Kamen, A. A. (2006) Production of adeno-associated viral vectors in insect cells using triple infection: optimization of baculovirus concentration ratios *Biotechnol Bioeng* 95, 1081-92.
17. Urabe, M., et al. (2006) Scalable generation of high-titer recombinant adeno-associated virus type 5 in insect cells *J Virol* 80, 1874-85.
18. Habib, S., et al. (1996) Bifunctionality of the AcMNPV homologous region sequence (hr1): enhancer and ori functions have different sequence requirements *DNA Cell Biol* 15, 737-47.
19. Lu, M., Farrell, P. J., Johnson, R. & Iatrou, K. (1997) A baculovirus (*Bombyx mori* nuclear polyhedrosis virus) repeat element functions as a powerful constitutive enhancer in transfected insect cells *J Biol Chem* 272, 30724-8.
20. Guarino, L. A. & Dong, W. (1994) Functional dissection of the *Autographa californica* nuclear polyhedrosis virus enhancer element hr5 *Virology* 200, 328-35.
21. Leisy, D. J. & Rohrmann, G. F. (2000) The *Autographa californica* nucleopolyhedrovirus IE-1 protein complex has two modes of specific DNA binding *Virology* 274, 196-202.
22. Rodems, S. M. & Friesen, P. D. (1993) The hr5 transcriptional enhancer stimulates early expression from the *Autographa californica* nuclear polyhedrosis virus genome but is not required for virus replication *J Virol* 67, 5776-85.
23. Ramachandran, A., et al. (2001) Novel Sp family-like transcription factors are present in adult insect cells and are involved in transcription from the polyhedrin gene initiator promoter *J Biol Chem* 276, 23440-9.
24. Rasheedi, S., Ramachandran, A., Ehtesham, N. Z. & Hasnain, S. E. (2007) Biochemical characterization of Sf9 Sp-family-like protein factors reveals interesting features *Arch Virol* 152, 1819-28.
25. Pereira, D. J. & Muzyczka, N. (1997) The cellular transcription factor SP1 and an unknown cellular protein are required to mediate Rep protein activation of the adeno-associated virus p19 promoter *J Virol* 71, 1747-56.
26. Pereira, D. J. & Muzyczka, N. (1997) The adeno-associated virus type 2 p40 promoter requires a proximal Sp1 interaction and a p19 CArG-like element to facilitate Rep transactivation *J Virol* 71, 4300-9.
27. Chisholm, G. E. & Henner, D. J. (1988) Multiple early transcripts and splicing of the *Autographa californica* nuclear polyhedrosis virus IE-1 gene *J Virol* 62, 3193-200.
28. O'Reily, D. R., Miller, L. K. & Luckow, V. A. (1994) *Baculovirus Expression Vectors: A Laboratory Manual*. (Oxford University Press, New York).
29. Chomczynski, P. & Rymaszewski, M. (2006) Alkaline polyethylene glycol-based method for direct PCR from bacteria, eukaryotic tissue samples, and whole blood *Biotechniques* 40, 454, 456, 458.
30. Harrison, R. L. & Jarvis, D. L. (2007) Transforming lepidopteran insect cells for continuous recombinant protein expression *Methods Mol Biol* 388, 299-316.
31. Buratowski, S. & Chodosh, L. A. (2001) Mobility shift DNA-binding assay using gel electrophoresis *Curr Protoc Mol Biol* Chapter 12, Unit 12 2.
32. d'Alencon, E., et al. (2004) A genomic BAC library and a new BAC-GFP vector to study the holocentric pest Spodoptera frugiperda *Insect Biochem Mol Biol* 34, 331-41.
33. Theilmann, D. A. & Stewart, S. (1991) Identification and characterization of the IE-1 gene of *Orgyia pseudotsugata* multicapsid nuclear polyhedrosis virus *Virology* 180, 492-508.
34. Rasmussen, C., Leisy, D. J., Ho, P. S. & Rohrmann, G. F. (1996) Structure-function analysis of the *Autographa californica* multinucleocapsid nuclear polyhedrosis virus homologous region palindromes *Virology* 224, 235-45.
35. Zolotukhin, S., et al. (1999) Recombinant adeno-associated virus purification using novel methods improves infectious titer and yield *Gene Ther* 6, 973-85.

*J. Virol*, 1995 69(1):156-165.

Baculovirus and Insect Cell Expression Protocols (chapter 6) By David W. Murhammer Contributor David W. Murhammer, Edition: 2, illustrated, Published by Humana Press, 2007, ISBN 1588295370, 9781588295378 discussing alternative cell lines that can be utilized in accordance with the teachings herein. The subject matter referenced in this cite is incorporated by reference.

In reviewing the detailed disclosure which follows, and the specification more generally, it should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

The invention claimed is:

1. An inducible protein expression system, said system comprising a baculovirus expression vector (BEV) that comprises a BEV-immediate early transcriptional transactivator inducer element (IE-1) and an AAV rep gene, wherein expression of the IE-1 and the AAV rep gene is under control of an expression control element; and an insect cell stably transformed with an expression cassette comprising a gene of interest, operatively linked to a promoter, an hr2 0.9 element, and a rep-binding element (RBE);

wherein expression of said gene of interest is induced upon infection of said insect cell with said BEV.

2. The system of claim 1, wherein the RBE element is upstream of the promoter.

3. The system of claim 1, wherein said expression cassette is integrated into a genome of said cell.

4. The system of claim 1, wherein said insect cell is an insect sf9 cell.

5. An inducible protein expression system, said system comprising a baculovirus expression vector (BEV) that comprises a BEV immediate early transcriptional transactivator inducer element (IE-1) whose expression is under control of an expression control element; and an insect cell stably transformed with an expression cassette comprising a gene of interest operatively linked to a promoter and an hr2 0.9 element;

wherein expression of the gene of interest is induced upon infection of said insect cell with said BEV and expression of the IE-1.

6. The system of claim 5, wherein said insect cell is an insect sf9 cell.

7. An inducible protein expression system, said system comprising a baculovirus expression vector (BEV) that comprises a BEV immediate early transactivator inducer element (IE-1), wherein expression of the IE-1 is under control of an expression control element; and an insect cell stably transformed with an expression cassette comprising a gene of interest and a AAV rep gene operatively linked to a promoter, an hr2 0.9 element, and a rep-binding element (RBE), wherein expression of said rep gene and said gene of interest is induced upon infection of said insect cell with said BEV; and rescue and amplification of said expression cassette is induced upon expression of said rep gene.

8. The system of claim 7, wherein said rep gene is upstream of said gene of interest.

9. The system of claim 7, wherein said expression cassette is integrated into a genome of said insect cell and is rescued therefrom and amplified upon expression of said rep gene.

* * * * *

SEQUENCE LISTING

<160> NUMBER OF SEQ ID NOS: 16

<210> SEQ ID NO 1
<211> LENGTH: 1866
<212> TYPE: DNA
<213> ORGANISM: Adeno-associated virus-2

<400> SEQUENCE: 1

```
atgccggggt tttacgagat tgtgattaag gtccccagcg accttgacga gcatctgccc      60
ggcatttctg acagctttgt gaactgggtg gccgagaagg aatgggagtt gccgccagat     120
tctgacatgg atctgaatct gattgagcag gcaccctga ccgtggccga gaagctgcag     180
cgcgactttc tgacggaatg gcgccgtgtg agtaaggccc cggaggccct tttctttgtg     240
caatttgaga agggagagag ctacttccac atgcacgtgc tcgtggaaac caccggggtg     300
aaatccatgg ttttgggacg tttcctgagt cagattcgcg aaaaactgat tcagagaatt     360
taccgcggga tcgagccgac tttgccaaac tggttcgcgg tcacaaagac cagaaatggc     420
gccggaggcg ggaacaaggt ggtggatgag tgctacatcc ccaattactt gctccccaaa     480
acccagcctg agctccagtg ggcgtggact aatatggaac agtatttaag cgcctgtttg     540
aatctcacgg agcgtaaacg gttggtggcg cagcatctga cgcacgtgtc gcagacgcag     600
gagcagaaca aagagaatca gaatcccaat tctgatgcgc cggtgatcag atcaaaaact     660
tcagccaggt acatggagct ggtcgggtgg ctcgtggaca aggggattac ctcggagaag     720
cagtggatcc aggaggacca ggcctcatac atctccttca atgcggcctc caactcgcgg     780
tcccaaatca aggctgcctt ggacaatgcg ggaaagatta tgagcctgac taaaaccgcc     840
cccgactacc tggtgggcca gcagcccgtg gaggacattt ccagcaatcg gatttataaa     900
attttggaac taaacgggta cgatcccaa tatgcggctt ccgtctttct gggatgggcc     960
acgaaaaagt tcggcaagag gaacaccatc tggctgtttg ggcctgcaac taccgggaag    1020
accaacatcg cggaggccat agcccacact gtgcccttct acgggtgcgt aaactggacc    1080
aatgagaact ttccctcaa cgactgtgtc gacaagatgg tgatctggtg ggaggagggg    1140
aagatgaccg ccaaggtcgt ggagtcggcc aaagccattc tcggaggaag caaggtgcgc    1200
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
```

-continued

```
ttgcaagacc ggatgttcaa atttgaactc acccgccgtc tggatcatga ctttgggaag    1380
gtcaccaagc aggaagtcaa agactttttc cggtgggcaa aggatcacgt ggttgaggtg    1440
gagcatgaat tctacgtcaa aaagggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc agacaggtac caaaacaaat gttctcgtca cgtgggcatg    1620
aatctgatgc tgtttccctg cagacaatgc gagagaatga atcagaattc aaatatctgc    1680
ttcactcacg gacagaaaga ctgtttagag tgctttcccg tgtcagaatc tcaacccgtt    1740
tctgtcgtca aaaaggcgta tcagaaactg tgctacattc atcatatcat gggaaaggtg    1800
ccagacgctt gcactgcctg cgatctggtc aatgtggatt tggatgactg catctttgaa    1860
caataa                                                                1866
```

<210> SEQ ID NO 2
<211> LENGTH: 621
<212> TYPE: PRT
<213> ORGANISM: Adeno-associated virus-2

<400> SEQUENCE: 2

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
```

|   |   |   | 275 |   |   | 280 |   |   |   | 285 |   |   |
|---|---|---|---|---|---|---|---|---|---|---|---|---|

Pro Val Glu Asp Ile Ser Ser Asn Arg Ile Tyr Lys Ile Leu Glu Leu
290                   295                   300

Asn Gly Tyr Asp Pro Gln Tyr Ala Ala Ser Val Phe Leu Gly Trp Ala
305                   310                   315                   320

Thr Lys Lys Phe Gly Lys Arg Asn Thr Ile Trp Leu Phe Gly Pro Ala
                  325                   330                   335

Thr Thr Gly Lys Thr Asn Ile Ala Glu Ala Ile Ala His Thr Val Pro
                  340                   345                   350

Phe Tyr Gly Cys Val Asn Trp Thr Asn Glu Asn Phe Pro Phe Asn Asp
                  355                   360                   365

Cys Val Asp Lys Met Val Ile Trp Trp Glu Glu Gly Lys Met Thr Ala
370                   375                   380

Lys Val Val Glu Ser Ala Lys Ala Ile Leu Gly Gly Ser Lys Val Arg
385                   390                   395                   400

Val Asp Gln Lys Cys Lys Ser Ser Ala Gln Ile Asp Pro Thr Pro Val
                  405                   410                   415

Ile Val Thr Ser Asn Thr Asn Met Cys Ala Val Ile Asp Gly Asn Ser
                  420                   425                   430

Thr Thr Phe Glu His Gln Gln Pro Leu Gln Asp Arg Met Phe Lys Phe
                  435                   440                   445

Glu Leu Thr Arg Arg Leu Asp His Asp Phe Gly Lys Val Thr Lys Gln
450                   455                   460

Glu Val Lys Asp Phe Phe Arg Trp Ala Lys Asp His Val Val Glu Val
465                   470                   475                   480

Glu His Glu Phe Tyr Val Lys Lys Gly Gly Ala Lys Lys Arg Pro Ala
                  485                   490                   495

Pro Ser Asp Ala Asp Ile Ser Glu Pro Lys Arg Val Arg Glu Ser Val
                  500                   505                   510

Ala Gln Pro Ser Thr Ser Asp Ala Glu Ala Ser Ile Asn Tyr Ala Asp
                  515                   520                   525

Arg Tyr Gln Asn Lys Cys Ser Arg His Val Gly Met Asn Leu Met Leu
530                   535                   540

Phe Pro Cys Arg Gln Cys Glu Arg Met Asn Gln Asn Ser Asn Ile Cys
545                   550                   555                   560

Phe Thr His Gly Gln Lys Asp Cys Leu Glu Cys Phe Pro Val Ser Glu
                  565                   570                   575

Ser Gln Pro Val Ser Val Val Lys Lys Ala Tyr Gln Lys Leu Cys Tyr
                  580                   585                   590

Ile His His Ile Met Gly Lys Val Pro Asp Ala Cys Thr Ala Cys Asp
                  595                   600                   605

Leu Val Asn Val Asp Leu Asp Asp Cys Ile Phe Glu Gln
610                   615                   620

<210> SEQ ID NO 3
<211> LENGTH: 1194
<212> TYPE: DNA
<213> ORGANISM: Adeno-associated virus-2

<400> SEQUENCE: 3

```
atggagctgg tcgggtggct cgtggacaag gggattacct cggagaagca gtggatccag    60
gaggaccagg cctcatacat ctccttcaat gcggcctcca actcgcggtc ccaaatcaag   120
gctgccttgg acaatgcggg aaagattatg agcctgacta aaaccgcccc cgactacctg   180
gtgggccagc agcccgtgga ggacatttcc agcaatcgga tttataaaat tttggaacta   240
```

```
aacgggtacg atccccaata tgcggcttcc gtctttctgg gatgggccac gaaaaagttc    300
ggcaagagga acaccatctg gctgtttggg cctgcaacta ccgggaagac caacatcgcg    360
gaggccatag cccacactgt gcccttctac gggtgcgtaa actggaccaa tgagaacttt    420
cccttcaacg actgtgtcga caagatggtg atctggtggg aggagggaa gatgaccgcc     480 aaggtcgtgg agtcggccaa agccattctc ggaggaagca aggtgcgcgt ggaccagaaa    540
tgcaagtcct cggcccagat agacccgact cccgtgatcg tcacctccaa caccaacatg    600
tgcgccgtga ttgacgggaa ctcaacgacc ttcgaacacc agcagccgtt gcaagaccgg    660
atgttcaaat ttgaactcac ccgccgtctg gatcatgact ttgggaaggt caccaagcag    720
gaagtcaaag acttttttcg gtgggcaaag gatcacgtgg ttgaggtgga gcatgaattc    780
tacgtcaaaa agggtggagc caagaaaaga cccgcccca gtgacgcaga tataagtgag     840
cccaaacggg tgcgcgagtc agttgcgcag ccatcgacgt cagacgcgga agcttcgatc    900
aactacgcag acaggtacca aaacaaatgt tctcgtcacg tgggcatgaa tctgatgctg    960
tttccctgca gacaatgcga gagaatgaat cagaattcaa atatctgctt cactcacgga   1020
cagaaagact gtttagagtg ctttcccgtg tcagaatctc aacccgtttc tgtcgtcaaa   1080
aaggcgtatc agaaactgtg ctacattcat catatcatgg gaaaggtgcc agacgcttgc   1140
actgcctgcg atctggtcaa tgtggatttg gatgactgca tctttgaaca ataa         1194
```

<210> SEQ ID NO 4
<211> LENGTH: 397
<212> TYPE: PRT
<213> ORGANISM: Adeno-associated virus-2

<400> SEQUENCE: 4

```
Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205
```

```
Thr Thr Phe Glu His Gln Gln Pro Leu Gln Asp Arg Met Phe Lys Phe
    210                 215                 220
Glu Leu Thr Arg Arg Leu Asp His Asp Phe Gly Lys Val Thr Lys Gln
225                 230                 235                 240
Glu Val Lys Asp Phe Phe Arg Trp Ala Lys Asp His Val Glu Val
                245                 250                 255
Glu His Glu Phe Tyr Val Lys Lys Gly Gly Ala Lys Lys Arg Pro Ala
            260                 265                 270
Pro Ser Asp Ala Asp Ile Ser Glu Pro Lys Arg Val Arg Glu Ser Val
        275                 280                 285
Ala Gln Pro Ser Thr Ser Asp Ala Glu Ala Ser Ile Asn Tyr Ala Asp
    290                 295                 300
Arg Tyr Gln Asn Lys Cys Ser Arg His Val Gly Met Asn Leu Met Leu
305                 310                 315                 320
Phe Pro Cys Arg Gln Cys Glu Arg Met Asn Gln Asn Ser Asn Ile Cys
                325                 330                 335
Phe Thr His Gly Gln Lys Asp Cys Leu Glu Cys Phe Pro Val Ser Glu
            340                 345                 350
Ser Gln Pro Val Ser Val Val Lys Lys Ala Tyr Gln Lys Leu Cys Tyr
        355                 360                 365
Ile His His Ile Met Gly Lys Val Pro Asp Ala Cys Thr Ala Cys Asp
    370                 375                 380
Leu Val Asn Val Asp Leu Asp Asp Cys Ile Phe Glu Gln
385                 390                 395

<210> SEQ ID NO 5
<211> LENGTH: 2208
<212> TYPE: DNA
<213> ORGANISM: Adeno-associated virus-2

<400> SEQUENCE: 5
atggctgccg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtacctcg gacccttcaa cggactcgac     180
aagggagagc cggtcaacga ggcagacgcc gcggccctcg agcacgacaa agcctacgac     240
cggcagctcg acagcggaga caaccccgta ctcaagtaca accacgccga cgcggagttt     300
caggagcgcc ttaaagaaga tacgtctttt gggggcaacc tcggacgagc agtcttccag     360
gcgaaaaaga gggttcttga acctctgggc ctggttgagg aacctgttaa acggctccg     420 ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg acccccagcc tctcggacag ccaccagcag cccctctgg tctgggaact     600 aatacgatgg ctacaggcag tggcgcacca atggcagaca taacgagggg cgccgacgga     660
gtgggtaatt cctcgggaaa ttggcattgc gattccacat ggatgggcga cagagtcatc     720
accaccagca cccgaacctg gcccctgccc acctacaaca accacctcta caaacaaatt     780
tccagccaat caggagcctc gaacgacaat cactactttg gctacagcac ccttgggggg     840
tattttgact tcaacagatt ccactgccac ttttcaccac gtgactggca agactcatc     900 aacaacaact ggggattccg acccaagaga ctcaacttca agctctttaa cattcaagtc     960
aaagaggtca cgcagaatga cggtacgacg acgattgcca ataacctta cagcacggtt    1020 caggtgttta ctgactcgga gtaccagctc ccgtacgtcc tcggctcggc gcatcaagga    1080
```

-continued

```
tgcctcccgc cgttcccagc agacgtcttc atggtgccac agtatggata cctcaccctg    1140
aacaacggga gtcaggcagt aggacgctct tcatttttact gcctggagta ctttccttct    1200
cagatgctgc gtaccggaaa caactttacc ttcagctaca cttttgagga cgttcctttc    1260
cacagcagct acgctcacag ccagagtctg accgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt ttcctcagag cggggttctc    1620
atctttggga agcaaggctc agagaaaaca atgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctcccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatccga aattcagtac    2100 acttccaact acaacaagtc tgttaatgtg gactttactg tggacactaa tggcgtgtat    2160
tcagagcctc gccccattgg caccagatac ctgactcgta atctgtaa                 2208
```

<210> SEQ ID NO 6
<211> LENGTH: 735
<212> TYPE: PRT
<213> ORGANISM: Adeno-associated virus-2

<400> SEQUENCE: 6

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
```

```
            180                 185                 190
Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605
```

| | | | | | | | | | | | |
|---|---|---|---|---|---|---|---|---|---|---|---|
| Arg | Asp | Val | Tyr | Leu | Gln | Gly | Pro | Ile | Trp | Ala | Lys | Ile | Pro | His | Thr |
| | 610 | | | | 615 | | | | 620 | | |

```
Arg Asp Val Tyr Leu Gln Gly Pro Ile Trp Ala Lys Ile Pro His Thr
    610                 615                 620

Asp Gly His Phe His Pro Ser Pro Leu Met Gly Phe Gly Leu Lys
625                 630                 635                 640

His Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 7
<211> LENGTH: 1749
<212> TYPE: DNA
<213> ORGANISM: Autographa californica nucleopolyhedrovirus

<400> SEQUENCE: 7

| | |
|---|---|
| atgacgcaaa ttaattttaa cgcgtcgtac accagcgctt cgacgccgtc ccgagcgtcg | 60 |
| ttcgacaaca gctattcaga gttttgtgat aaacaaccca cgactatttt aagttattat | 120 |
| aaccatccca ccccggatgg agccgacacg gtgatatctg acagcgagac tgcggcagct | 180 |
| tcaaactttt tggcaagcgt caactcgtta actgataatg attttagtgga atgtttgctc | 240 |
| aagaccactg ataatctcga agaagcagtt agttctgctt attattcgga atcccttgag | 300 |
| cagcctgttg tggagcaacc atcgcccagt tctgcttatc atgcggaatc ttttgagcat | 360 |
| tctgctggtg tgaaccaacc atcggcaact ggaactaaac ggaagctgga cgaatacttg | 420 |
| gacaattcac aaggtgtggt gggccagttt aacaaaatta aattgaggcc taaatacaag | 480 |
| aaaagcacaa ttcaaagctg tgcaacccct gaacagacaa ttaatcacaa acgaacatt | 540 |
| tgcacggtcg cttcaactca agaaattacg cattatttta ctaatgattt tgcgccgtat | 600 |
| ttaatgcgtt cgacgacaa cgactacaat tccaacaggt tctccgacca tatgtccgaa | 660 |
| actggttatt acatgtttgt ggttaaaaaa agtgaagtga agccgtttga aattatattt | 720 |
| gccaagtacg tgagcaatgt ggtttacgaa tatacaaaca attattacat ggtagataat | 780 |
| cgcgtgtttg tggtaacttt tgataaaatt aggtttatga tttcgtacaa tttggttaaa | 840 |
| gaaaccggca tagaaattcc tcattctcaa gatgtgtgca acgacgagac ggctgcacaa | 900 |
| aattgtaaaa atgccatttt cgtcgatgtg caccacacgt ttaaagctgc tctgacttca | 960 |
| tatttttaatt tagatatgta ttacgcgcaa accacatttg tgactttgtt acaatcgttg | 1020 |
| ggcgaaagaa aatgtgggtt tcttttgagc aagttgtacg aaatgtatca agataaaaat | 1080 |
| ttatttactt tgcctattat gcttagtcgt aaagagagta tgaaattga gactgcatct | 1140 |
| aataatttct ttgtatcgcc gtatgtgagt caaatattaa agtattcgga aagtgtgcag | 1200 |
| tttcccgaca atcccccaaa caaatatgtg gtggacaatt taaatttaat tgttaacaaa | 1260 |
| aaaagtacgc tcacgtacaa atacagcagc gtcgctaatc ttttgtttaa taattataaa | 1320 |
| tatcatgaca atattgcgag taataataac gcagaaaatt taaaaaaggt taagaaggag | 1380 |
| gacggcagca tgcacattgt cgaacagtat ttgactcaga atgtagataa tgtaaagggt | 1440 |

```
cacaatttta tagtattgtc tttcaaaaac gaggagcgat tgactatagc taagaaaaac    1500
aaagagtttt attggatttc tggcgaaatt aaagatgtag acgttagtca agtaattcaa    1560
aaatataata gatttaagca tcacatgttt gtaatcggta aagtgaaccg aagagagagc    1620
actacattgc acaataattt gttaaaattg ttagctttaa tattacaggg tctggttccg    1680
ttgtccgacg ctataacgtt tgcggaacaa aactaaatt gtaaatataa aaaattcgaa     1740
tttaattaa                                                            1749
```

```
<210> SEQ ID NO 8
<211> LENGTH: 582
<212> TYPE: PRT
<213> ORGANISM: Autographa californica nucleopolyhedrovirus

<400> SEQUENCE: 8

Met Thr Gln Ile Asn Phe Asn Ala Ser Tyr Thr Ser Ala Ser Thr Pro
1               5                   10                  15

Ser Arg Ala Ser Phe Asp Asn Ser Tyr Ser Glu Phe Cys Asp Lys Gln
            20                  25                  30

Pro Asn Asp Tyr Leu Ser Tyr Tyr Asn His Pro Thr Pro Asp Gly Ala
        35                  40                  45

Asp Thr Val Ile Ser Asp Ser Glu Thr Ala Ala Ser Asn Phe Leu
    50                  55                  60

Ala Ser Val Asn Ser Leu Thr Asp Asn Asp Leu Val Glu Cys Leu Leu
65                  70                  75                  80

Lys Thr Thr Asp Asn Leu Glu Glu Ala Val Ser Ser Ala Tyr Tyr Ser
                85                  90                  95

Glu Ser Leu Glu Gln Pro Val Val Gln Pro Ser Pro Ser Ser Ala
            100                 105                 110

Tyr His Ala Glu Ser Phe Glu His Ser Ala Gly Val Asn Gln Pro Ser
        115                 120                 125

Ala Thr Gly Thr Lys Arg Lys Leu Asp Glu Tyr Leu Asp Asn Ser Gln
    130                 135                 140

Gly Val Val Gly Gln Phe Asn Lys Ile Lys Leu Arg Pro Lys Tyr Lys
145                 150                 155                 160

Lys Ser Thr Ile Gln Ser Cys Ala Thr Leu Glu Gln Thr Ile Asn His
                165                 170                 175

Asn Thr Asn Ile Cys Thr Val Ala Ser Thr Gln Glu Ile Thr His Tyr
            180                 185                 190

Phe Thr Asn Asp Phe Ala Pro Tyr Leu Met Arg Phe Asp Asp Asn Asp
        195                 200                 205

Tyr Asn Ser Asn Arg Phe Ser Asp His Met Ser Glu Thr Gly Tyr Tyr
    210                 215                 220

Met Phe Val Val Lys Lys Ser Glu Val Lys Pro Phe Glu Ile Ile Phe
225                 230                 235                 240

Ala Lys Tyr Val Ser Asn Val Val Tyr Glu Tyr Thr Asn Asn Tyr Tyr
                245                 250                 255

Met Val Asp Asn Arg Val Phe Val Thr Phe Asp Lys Ile Arg Phe
            260                 265                 270

Met Ile Ser Tyr Asn Leu Val Lys Glu Thr Gly Ile Glu Ile Pro His
        275                 280                 285

Ser Gln Asp Val Cys Asn Asp Glu Thr Ala Ala Gln Asn Cys Lys Lys
    290                 295                 300

Cys His Phe Val Asp Val His His Thr Phe Lys Ala Ala Leu Thr Ser
305                 310                 315                 320
```

```
Tyr Phe Asn Leu Asp Met Tyr Ala Gln Thr Thr Phe Val Thr Leu
            325                 330                 335

Leu Gln Ser Leu Gly Glu Arg Lys Cys Gly Phe Leu Leu Ser Lys Leu
        340                 345                 350

Tyr Glu Met Tyr Gln Asp Lys Asn Leu Phe Thr Leu Pro Ile Met Leu
            355                 360                 365

Ser Arg Lys Glu Ser Asn Glu Ile Glu Thr Ala Ser Asn Asn Phe Phe
370                 375                 380

Val Ser Pro Tyr Val Ser Gln Ile Leu Lys Tyr Ser Glu Ser Val Gln
385                 390                 395                 400

Phe Pro Asp Asn Pro Pro Asn Lys Tyr Val Val Asp Asn Leu Asn Leu
                405                 410                 415

Ile Val Asn Lys Lys Ser Thr Leu Thr Tyr Lys Tyr Ser Ser Val Ala
            420                 425                 430

Asn Leu Leu Phe Asn Asn Tyr Lys Tyr His Asp Asn Ile Ala Ser Asn
        435                 440                 445

Asn Asn Ala Glu Asn Leu Lys Lys Val Lys Lys Glu Asp Gly Ser Met
450                 455                 460

His Ile Val Glu Gln Tyr Leu Thr Gln Asn Val Asp Asn Val Lys Gly
465                 470                 475                 480

His Asn Phe Ile Val Leu Ser Phe Lys Asn Glu Glu Arg Leu Thr Ile
                485                 490                 495

Ala Lys Lys Asn Lys Glu Phe Tyr Trp Ile Ser Gly Glu Ile Lys Asp
            500                 505                 510

Val Asp Val Ser Gln Val Ile Gln Lys Tyr Asn Arg Phe Lys His His
            515                 520                 525

Met Phe Val Ile Gly Lys Val Asn Arg Arg Glu Ser Thr Thr Leu His
        530                 535                 540

Asn Asn Leu Leu Lys Leu Leu Ala Leu Ile Leu Gln Gly Leu Val Pro
545                 550                 555                 560

Leu Ser Asp Ala Ile Thr Phe Ala Glu Gln Lys Leu Asn Cys Lys Tyr
                565                 570                 575

Lys Lys Phe Glu Phe Asn
            580

<210> SEQ ID NO 9
<211> LENGTH: 669
<212> TYPE: DNA
<213> ORGANISM: Autographa californica nucleopolyhedrovirus

<400> SEQUENCE: 9
gctttacgag tagaattcta cgtgtaaaac ataatcaaga gatgatgtca tttgtttttc      60
aaaactgaac tcaagaaatg atgtcatttg ttttcaaaa ctgaactggc tttacgagta     120
gaattctact tgtaacgcat gatcaaggga tgatgtcatt tgttttcaa aaccgaactc     180 gctttacgag tagaattcta cttgtaaaac ataatcgaaa gatgatgtca tttgtttttt     240
aaaattgaac tggctttacg agtagaattc tacttgtaaa acacaatcga gagatgatgt     300
catattttgc acacggctct aattaaactc gctttacgag taaaattcta cttgtaacgc     360
atgatcaagg gatgatgtat tggatgagtc atttgttttt caaaactaaa ctcgctttac     420
gagtagaatt ctacttgtaa cgcacgccca agggatgatg tcattatttt gtgcaaagct     480
gatgtcatct tttgcacacg attataaaca caatcaaata atgactcatt gttttttcaa     540
aactgaactc gctttacgag tagaattcta cttgtaaaac acaatcaagc gatgatgtca     600
ttttaaaaat gatgtcattt gttttttcaaa actaaactcg ctttacgagt agaattctac    660
```

| | |
|---|---|
| gtgtaaaac | 669 |

<210> SEQ ID NO 10
<211> LENGTH: 150
<212> TYPE: DNA
<213> ORGANISM: Adeno-associated virus-2

<400> SEQUENCE: 10

| | |
|---|---|
| gccggaggcg ggaacaaggt ggtggatgag tgctacatcc ccaattactt gctccccaaa | 60 |
| acccagcctg agctccagtg ggcgtggact aatatggaac agtatttaag cgcctgtttg | 120 |
| aatctcacgg agcgtaaacg gttggtggcg | 150 |

<210> SEQ ID NO 11
<211> LENGTH: 989
<212> TYPE: DNA
<213> ORGANISM: Autographa californica nucleopolyhedrovirus

<400> SEQUENCE: 11

| | |
|---|---|
| tgagcaaaac acaaccggca aattctcggc ggccgtttgg gaatgcggaa taattgccat | 60 |
| atgtaaatga tgtcatcggt tctaactcgc tttacgagta gaattctacg tgtaaaacat | 120 |
| aatcaagaga tgatgtcatt tgttttcaa aactgaactc aagaaatgat gtcatttgtt | 180 |
| tttcaaaact gaactggctt tacgagtaga attctacttg taaaacacaa tcgagagatg | 240 |
| atgtcatatt ttgcacacgg ctctaattaa actcgcttta cgagtaaaat tctacttgta | 300 |
| acgcatgatc aagggatgat gtcattggat gagtcatttg tttttcaaaa ctaaactcgc | 360 |
| tttacgagta gaattctact tgtaaaacac aatcaaggga tgatgtcatt atacaaatga | 420 |
| tgtcatttgt ttttcaaaac taaactcgct ttacgggtag aattctactt gtaaaacagc | 480 |
| aactcgaggg atgatgtcat cctttactcg atgattataa acgtgtttat gtatgactca | 540 |
| tttgtttttc aaaactaaac tcgctttacg agtagattct acttgtaacg cacgatcaag | 600 |
| ggatgatgtc atttatttgt gcaaagctcg atgtcatctt ttgcacacga ttataaacac | 660 |
| aatccaaata atgactcatt tgttttcaaa actgaactcg ctttacgagt agaattctac | 720 |
| ttgtaaaaca caatcaaggg atgatgtcat tttcaaaatg atgtcatttg ttttttcaaaa | 780 |
| ctaaactcgc tttacgagta gaattctact tgtaaaacac aatcaaggga tgatgtcatt | 840 |
| taaaaatga tcatttgttt ttcaaaacta aactcgcttt acgagtagaa ttctacgtgt | 900 |
| aaaacacaat caaggatga tgtcatttac taaataaaat aattatttaa ataaaactgt | 960 |
| tttttattgt caaatacaca ttgattcac | 989 |

<210> SEQ ID NO 12
<211> LENGTH: 967
<212> TYPE: DNA
<213> ORGANISM: Autographa californica nucleopolyhedrovirus

<400> SEQUENCE: 12

| | |
|---|---|
| ggccgcgaat tcactagtga ttgcggaata attgccatat gtaaatgatg tcatcgttct | 60 |
| aactcgcttt acgagtagaa ttctacgtgt aaaacataat caagagatga tgtcatttgt | 120 |
| ttttcaaaac tgaactcaag aaatgatgtc atttgttttt caaaactgaa ctggctttac | 180 |
| gagcagaatt ctacttgtaa cgcatgatca agggatgatg tcatttgttt tttaaaattg | 240 |
| aactggcttt acgagtagaa ttctacttgt aaaacacaat cgagagatga tgtcatattt | 300 |
| tgcacacggc tctaattaaa ctcgctttac gagtaaaatt ctacttgtaa cgcatgatca | 360 |
| agggatgatg tcattggatg agtcatttgt ttttcaaaac taaactcgct ttacgagtag | 420 |

```
aattctactt gtaaaacaca atcaagggat gatgtcatta tacaaatgat gtcatttgtt    480
tttcaaaact aaactcgctt tacgggtaga attctacttg taaaacacaa tcgagggatg    540
atgtcatcct ttacacatga ttataaacgt gtttatgtat gactcatttg tttttcaaaa    600
ctaaactcgc tttacgagta gaattctact tgtaacgcac gatcaaggga tgatgtcatt    660
tatttgtgca aagctgatgt catcttttgc acacgattat aaacacaatc aaataatgac    720
tcatttgttt tcaaaactga actcgcttta cgagtagaat tctacttgta aaacacaatc    780
aagggatgat gtcattttaa aaatgatgtc atttgttttt caaaactaaa ctcgctttac    840
gagtagaatt ctacgtgtaa aacacaatca agggatgatg tcatttacta aaataaaata    900
attatttaaa taaaaatgtt tttattgtaa aatacacatt gattacacgt gacaatcgaa    960
ttcccgc                                                             967

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gatgatgtca tcctttatgc atgattataa acgtg                                35

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cacgtttata atcatgcata aaggatgaca tcatc                                35

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcagaattct acttgtaatg catgatcaag ggatg                                35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
catcccttga tcatgcgtta caagtagaat tctgc                                35
```